United States Patent
Terakawa et al.

(10) Patent No.: US 9,376,688 B2
(45) Date of Patent: Jun. 28, 2016

(54) METHOD OF PRODUCING CYCLAMEN WITH MULTI-PETALED FLOWERS

(75) Inventors: Teruhiko Terakawa, Atsugi (JP); Tomomichi Yamamura, Tokyo (JP); Masao Sugiyama, Atsugi (JP); Masaru Takagi, Tsukuba (JP); Nobutaka Mitsuda, Tsukuba (JP)

(73) Assignees: HOKKO CHEMICAL INDUSTRY CO., LTD., Tokyo (JP); NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 890 days.

(21) Appl. No.: 13/516,505

(22) PCT Filed: Dec. 16, 2010

(86) PCT No.: PCT/JP2010/072696
§ 371 (c)(1), (2), (4) Date: Jun. 15, 2012

(87) PCT Pub. No.: WO2011/074646
PCT Pub. Date: Jun. 23, 2011

(65) Prior Publication Data
US 2012/0331591 A1    Dec. 27, 2012

(30) Foreign Application Priority Data
Dec. 17, 2009  (JP) ................. 2009-286703

(51) Int. Cl.
C12N 15/82    (2006.01)
C12N 15/29    (2006.01)

(52) U.S. Cl.
CPC .......... *C12N 15/827* (2013.01); *C12N 15/8216* (2013.01)

(58) Field of Classification Search
USPC ........................................ 800/278
See application file for complete search history.

(56) References Cited

U.S. PATENT DOCUMENTS 7,342,148 B2    3/2008  Takagi et al.
2005/0044596 A1*  2/2005  Smith ..................... 800/303

FOREIGN PATENT DOCUMENTS

| JP | 2001-269176 A | 10/2001 |
| JP | 2001-269177 A | 10/2001 |
| JP | 2001-269178 A | 10/2001 |
| JP | 2001-269179 A | 10/2001 |
| JP | 2001-292776 A | 10/2001 |
| JP | 2001-292777 A | 10/2001 |
| JP | 2005-192483 A | 7/2005 |

(Continued)

OTHER PUBLICATIONS

Mitsuda et al. Efficient production of male and female sterile plants by expressin of a chimeric repressor in *Arabidopsis* and rice. Plant Biotechnology Journal. 2006. 4: 325-332.*

(Continued)

*Primary Examiner* — Shubo (Joe) Zhou
*Assistant Examiner* — Ashley K Buran
(74) *Attorney, Agent, or Firm* — Birch, Stewart, Kolasch & Birch, LLP

(57) ABSTRACT

A method of producing a multi-petaled *cyclamen* plant having an increased number of petals, including at least inhibiting the function of a transcription factor involved in morphogenesis of a floral organ of *cyclamen*.

4 Claims, 2 Drawing Sheets

(a)

(b)

(c)

(56) References Cited

FOREIGN PATENT DOCUMENTS

| JP | 2006-42729 A | 2/2006 |
|---|---|---|
| WO | 03/055903 A1 | 7/2003 |

OTHER PUBLICATIONS

Koncz et al. T-DNA insertional mutagenesis in *Arabidopsis*. Plant Molecular Biology. 1992. 20: 963-976.*

Yellina et al. Floral homeotic C function genes repress specific B function genes in the carpel whorl of the basal eudicot California poppy (Eschscholzia californica). EvoDevo. 2010. 1(13): 1-13.*

Narumi et al. Chimeric AGAMOUS repressor induces serrated petal type phenotype in Torenia fournieri similar to that induced by cytokinin application. Plant Biotechnology. 2008. 25: 45-53.*

Blasdale, "Cyclamen Persicum: It's Natural and Cultivated Forms," Stanford University Press, 1954, pp. 39-41, XP009169133.

Extended European Search Report dated May 14, 2013 for European Application No. 10837671.6.

Gutierrez-Cortines et al., "Beyond the ABCs: ternary complex formation in the control of floral organ identity," Trends in Plant Science, vol. 5, No. 11, Nov. 2000, pp. 471-476, XP055061055.

Theissen, "Flower Development, Genetics of," Encyclopedia of genetics, 2001, pp. 713-717, XP055061057.

UNIPROT, Data Base Accession No. B5UB74, Nov. 25, 2008, 1 page, XP002696076.

International Search Report, dated Jan. 18, 2011, issued in PCT/JP2010/072696.

Shikata et al., Brain techno news, No. 134, pp. 11-15, Jul. 15, 2009.

Tanaka et al., 51st Proceedings of the Annual Meeting of the Japanese Society of Plant Physiologists, p. 198, 4pB06(383), Mar. 12, 2010.

Terakawa et al., 25th Annual Meeting of the Japanese Society for Plant Cell and Molecular Biology, p. 40, Aug. 8, 2007.

Terakawa et al., 51st Proceedings of the Annual Meeting of the Japanese Society of Plant Physiologists, p. 198, 4pB07 (384), Mar. 12, 2010.

Takako Narumi et al., "Chimeric AGAMOUS repressor induces serrated petal phenotype in Torenia fournieri similar to that induced by cytokinin application", Plant Biotechnology, vol. 25, pp. 45-53, 2008.

* cited by examiner (a) (b)

(a) (b)

(a) (b) (c)

(a) (b)

METHOD OF PRODUCING CYCLAMEN WITH MULTI-PETALED FLOWERS

TECHNICAL FIELD

The present invention relates to a method of producing *cyclamen* with multi-petaled flowers.

BACKGROUND ART

The morphology of floral organs is an important factor for enhancing the decorative properties of ornamental plants. With regard to the morphogenesis of the floral organs, first, an inflorescence meristem differentiates into a flower primordium, and then a floral meristem contained in the flower primordium differentiates into four types of floral organs, namely, sepals, petals, stamens and pistils. Thereafter, a mature flower is formed as a complex organ including the floral organs.

A flower that is generally called "double-flowered" implies that the flower is a state in which more petals further line up at the inner side of petals, where stamens or pistils line up, and it seems as if the flower is constituted only of petals.

In general, the morphogenesis of the flower in higher plants may be explained by the ABC model. In the ABC model, the morphological change of the flower is explained by the transcriptional regulation of genes that belong to the MADS-box family (Non-Patent Literature 1). The MADS-box family is a gene family consisting of 30 or more kinds of genes, and the family is further divided into Class A, Class B and Class C. The genes that belong to the MADS-box family encode transcription factors containing a conserved region called the MADS-box. Genes such as APETALA1 (AP1) and APETALA (AP2) are classified as Class A genes; genes such as APETALA3 (AP3) and PISTILLATA (PI) are classified as Class B genes; and genes such as AGAMOUS (AG) are classified as Class C genes. It has been confirmed that variants of these genes present morphological changes of the flower.

Plants in which the morphology of petals or the number of petals has been modified have been hitherto obtained mainly by cross breeding of crossing varieties of plants, or by searching for mutants that occur in nature. However, in the case of cross breeding, a long time and skilled technicians are needed in order to produce plants having a desired morphology, and in the case of the search for mutants, the desired morphology is obtained only incidentally, there is a demand for a simple and easy method for reliably modifying the morphology of petals or the number of petals.

As the method for modifying the morphology of a plant by genetic engineering, methods of utilizing a functional peptide which converts an arbitrary transcription factor into a transcriptional repressor are known (Patent Literatures 1 to 7). These functional peptides are peptides excised from Class II ERF (Ethylene Responsive Element Binding Factor) protein, or from a plant zinc finger protein such as *Arabidopsis thaliana* SUPERMAN protein, and those peptides have simple structures. It has been reported in connection with *Arabidopsis thaliana* that the expression of AP3 gene or AG gene are inhibited by introducing a DNA that encodes a chimeric protein which is a fusion protein of AP3 protein or AG protein, and a functional peptide, into the plant, and thereby sterile males are produced or the number of petals is increased (Patent Literatures 8 and 9).

However, since *Arabidopsis thaliana* is an ornamental plant having only one type of AG gene, it can be contemplated that functions of the AG gene of *Arabidopsis thaliana* may be different from functions of AG genes of ornamental plants having plural AG genes. In fact, it has been reported that a chimeric protein obtained by fusing an AG protein of *Arabidopsis thaliana* and a functional peptide is not able to increase the number of petals in torenia (Non-Patent Literature 2). Furthermore, it is also known that the functions of various AG genes in ornamental plants having plural AG genes may be different depending on the type of the ornamental plant.

*Cyclamen* is popular as an ornamental plant for decorative purposes. However, there is no report on the AG gene of *cyclamen*, and nothing is known about the number and functions of the AG gene of *cyclamen*.

PRIOR ART LITERATURE

Patent Literatures

Patent Literature 1: JP-A-2001-269177 ("JP-A" means unexamined published Japanese patent application)
Patent Literature 2: JP-A-2001-269178
Patent Literature 3: JP-A-2001-292776
Patent Literature 4: JP-A-2001-292777
Patent Literature 5: JP-A-2001-269176
Patent Literature 6: JP-A-2001-269179
Patent Literature 7: WO 03/055903 A
Patent Literature 8: JP-A-2005-192483
Patent Literature 9: JP-A-2006-42729

Non-Patent Literatures

Non-Patent Literature 1: Molecular Genetics of Flower Morphogenesis, "Molecular Mechanisms of Morphology Determination in Plants", New Edition (Shujunsha Co., Ltd.), 150-163, 2000
Non-Patent Literature 2: Plant Biotechnology 2008 25, 45-53

SUMMARY OF INVENTION

The present invention is contemplated for providing a method of producing multi-petaled *cyclamen* having an increased number of petals. Further, the present invention is contemplated for providing a *cyclamen* plant obtainable by the production method described above.

The inventors of the present invention succeeded in isolating two types of *cyclamen*-derived AG genes. Furthermore, the inventors of the present invention found that the number of petals of *cyclamen* is increased by inhibiting the expression of the genes. The present invention was completed based on this finding.

According to the present invention, the following means are provided.

[1] A method of producing a multi-petaled *cyclamen* plant having an increased number of petals, including at least inhibiting the function of a transcription factor involved in morphogenesis of a floral organ of *cyclamen*.
[2] The production method as described in the item [1], wherein the transcription factor has the amino acid sequence defined in any one of the following (a) to (c):
(a) the amino acid sequence of SEQ ID NO: 2,
(b) an amino acid sequence including substitution, deletion, insertion and/or addition of one or several amino acids in the amino acid sequence of SEQ ID NO: 2, and
(c) an amino acid sequence sharing 90% or more identity with the amino acid sequence of SEQ ID NO: 2.
[3] The production method as described in the item [2], further including inhibiting the function of a transcription factor which is involved in morphogenesis of a floral organ of *cyclamen* and has the amino acid sequence defined in any one of the following (d) to (f):

(d) the amino acid sequence of SEQ ID NO: 4, (e) an amino acid sequence including substitution, deletion, insertion and/or addition of one or several amino acids in the amino acid sequence of SEQ ID NO: 4, and (f) an amino acid sequence sharing 90% or more identity with the amino acid sequence of SEQ ID NO: 4.

[4] The production method as described in the item [1], wherein the transcription factor has the amino acid sequence defined in any one of the following (d) to (f):

(d) the amino acid sequence of SEQ ID NO: 4, (e) an amino acid sequence including substitution, deletion, insertion and/or addition of one or several amino acids in the amino acid sequence of SEQ ID NO: 4, and (f) an amino acid sequence sharing 90% or more identity with the amino acid sequence of SEQ ID NO: 4.

[5] A method of producing a multi-petaled *cyclamen* plant having an increased number of petals, including at least inhibiting the function of a transcription factor which is involved in the morphogenesis of a floral organ of *cyclamen* and has the amino acid sequence defined in any one of the following (d) to (f):

(d) the amino acid sequence of SEQ ID NO: 4, (e) an amino acid sequence including substitution, deletion, insertion and/or addition of one or several amino acids in the amino acid sequence of SEQ ID NO: 4, and (f) an amino acid sequence sharing 90% or more identity with the amino acid sequence of SEQ ID NO: 4, in a mutant of *cyclamen* in which the function of a transcription factor, which is involved in the morphogenesis of a floral organ of *cyclamen* and has the amino acid sequence defined in any one of the following (a) to (c), is inhibited:

(a) the amino acid sequence of SEQ ID NO: 2, (b) an amino acid sequence including substitution, deletion, insertion and/or addition of one or several amino acids in the amino acid sequence of SEQ ID NO: 2, and (c) an amino acid sequence sharing 90% or more identity with the amino acid sequence of SEQ ID NO: 2.

[6] The production method as described in any one of the items [1] to [5], wherein the function of the transcription factor is inhibited by using a chimeric protein obtained by fusing the transcription factor and a functional peptide which converts a transcription factor into a transcription repressor.

[7] The production method as described in the item [6], wherein the functional peptide is a peptide having any one of the amino acid sequences of SEQ ID NOS: 5 to 44.

[8] A *cyclamen* plant produced by the production method as described in any one of the items [1] to [7].

According to the production method of the present invention, a multi-petaled *cyclamen* having an increased number of petals as compared to wild type *cyclamen* can be efficiently produced. Furthermore, since a *cyclamen* having an increased number of petals can be obtained conveniently and reliably in a short time period, the efforts required in the breed improvement can be reduced to a large extent, as compared to cross breeding or a search for mutants.

Other and further features and advantages of the invention will appear more fully from the following description, appropriately referring to the accompanying drawings.

MODE FOR CARRYING OUT INVENTION

Figure 1:
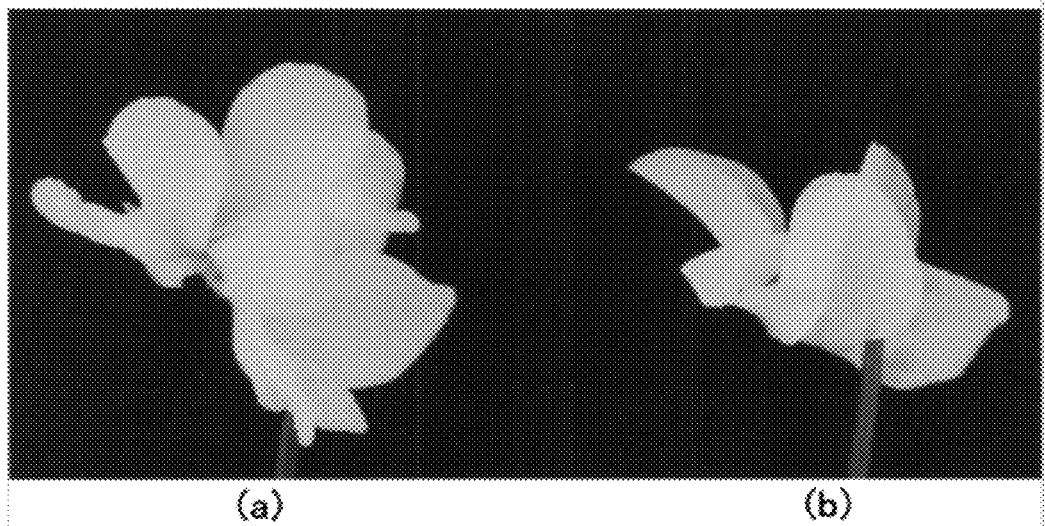
FIG. 1 illustrates the photographs of (a) the floral organs of a Melody White which has been transformed with CpAG1SRDX; and (b) the floral organs of a Melody White which has not been transformed. A is a side view photograph of the floral organs, and B is a front view photograph of the floral organs.
Figure 1:
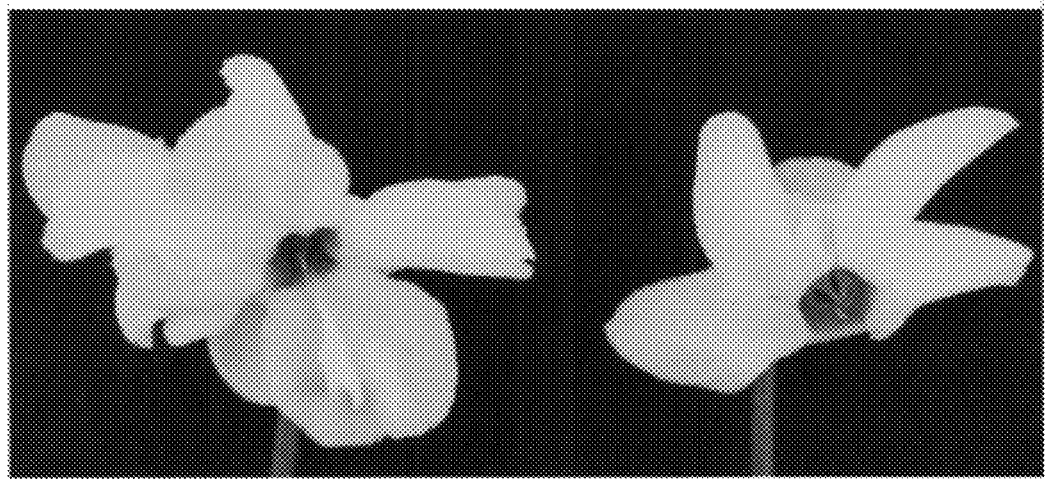

Hereinafter, the present invention will be described in detail based on preferred embodiments of the invention, but the present invention is not intended to be limited to these.

(1) Transcription Factor Involved in Morphogenesis of Floral Organs of *Cyclamen*

In the present invention, the term "transcription factor involved in morphogenesis of floral organs of *cyclamen*" means a transcription factor which regulates the expression of a gene that affects morphology of the floral organs in the process of formation of the floral organs of *cyclamen*, and preferably, which regulates the expression of a gene that involved in morphogenesis of the floral organs such as stamens and pistils. Examples of such a transcription factor include AGAMOUS (AG) proteins which belong to Class C of the MADS-box family, and among them, AGAMOUS 1 (AG1) protein and AGAMOUS 2 (AG2) protein are preferred.

AG1 protein is preferably a protein having the amino acid sequence of SEQ ID NO: 2, and AG1 protein may also be a protein having an amino acid sequence which includes substitution, deletion, insertion, and/or addition of one or several amino acids in the amino acid sequence of SEQ ID NO: 2, or a protein having an amino acid sequence sharing an identity of 80% or more, preferably 90% or more, more preferably 95% or more, and particularly preferably 97% or more with the amino acid sequence of SEQ ID NO: 2.

Furthermore, AG1 protein is preferably a protein encoded by a DNA having the nucleotide sequence extending from the nucleotide number 111 to the nucleotide number 851 of the nucleotide sequence of SEQ ID NO: 1, and may also be a protein encoded by a DNA having the nucleotide sequence of a DNA which is hybridizable with a DNA having a nucleotide sequence complementary to the nucleotide sequence extending from the nucleotide number 111 to the nucleotide number 851 of the nucleotide sequence of SEQ ID NO: 1 under stringent conditions.

AG2 protein is preferably a protein having the amino acid sequence of SEQ ID NO: 4, and AG2 protein may also be a protein having an amino acid sequence which includes substitution, deletion, insertion, and/or addition of one or several amino acids in the amino acid sequence of SEQ ID NO: 4, or a protein having an amino acid sequence which shares an identity of 80% or more, preferably 90% or more, more preferably 95% or more, and particularly preferably 97% or more with the amino acid sequence of SEQ ID NO: 4.

Furthermore, AG2 protein is preferably a protein encoded by a DNA having a nucleotide sequence extending from the nucleotide number 87 to the nucleotide number 830 of the nucleotide sequence of SEQ ID NO: 3, and may also be a protein encoded by a DNA having the nucleotide sequence of a DNA which is hybridizable with a DNA having a nucleotide sequence complementary to the nucleotide sequence extending from the nucleotide number 87 to the nucleotide number 830 of the nucleotide sequence of SEQ ID NO: 3 under stringent condition.

In the present invention, the term "one or several" means preferably 1 to 30, more preferably 1 to 20, more preferably 1 to 10, more preferably 1 to 7, even more preferably 1 to 5, and particularly preferably 1 to 3.

In the present invention, the term "identity (%) of the amino acid sequence" means the maximum identity (%) between two amino acid sequences to be compared, which is obtained by aligning the two amino acid sequences while introducing, as necessary, gaps thereinto (alignment). The alignment for the purpose of determining the identity between amino acid sequences can be carried out using conventional methods, and for example, publicly available computer software such as BLAST, or commercially available software such as DNASIS Pro (Hitachi Software Engineering Co., Ltd) and GENETYX (Genetyx Corp.) can also be used.

In the present invention, the term "stringent conditions" means the conditions under which DNAs sharing a high identity in the nucleotide sequences, for example, DNAs sharing an identity of 80% or more, preferably 90% or more, more preferably 95% or more, and particularly preferably 97% or more are hybridized, while DNAs sharing an identity lower than the above-described range are not hybridized, or the conditions of washing once, and more preferably two or three times, at a temperature and a salt concentration corresponding to 60° C., 1×SSC and 0.1% SDS; preferably 60° C., 0.1×SSC and 0.1% SDS; more preferably 65° C., 0.1×SSC and 0.1% SDS, and even more preferably 68° C., 0.1×SSC and 0.1% SDS, which are the washing conditions for conventional Southern hybridization. The hybridization can be carried out by a known method, such as a method described in J. Sambrook, et al., Molecular Cloning, A Laboratory Manual, 2nd Ed., Cold Spring Harbor Laboratory (1989).

(2) Inhibition of Transcription Factor Function and Production of Multi-Petaled *Cyclamen*

According to the present invention, the function of the transcription factor involved in the morphogenesis of the floral organs of *cyclamen* is inhibited in the *cyclamen* plant. There are no particular limitations on the method of inhibiting the function of the transcription factor, and examples thereof include a method of introducing a transcriptional repressor into a *cyclamen* plant; a method of destroying the gene that encodes the transcription factor; and a method of inhibiting the expression of a gene encoding the transcription factor by RNA interference (RNAi) or the like. Among them, a method of introducing a transcriptional repressor into the plant is preferred. The transcriptional repressor is preferably, for example, a chimeric protein obtained by fusing a transcription factor and a functional peptide having a function to convert a transcription factor into a transcriptional repressor. A DNA encoding the chimeric protein is introduced into the plant, the chimeric protein is produced in the plant, and thereby the function of the transcription factor can be inhibited.

In the present invention, the term "functional peptide having a function to convert a transcription factor into a transcriptional repressor" means a functional peptide which converts an arbitrary transcription factor into a transcription repressor (hereinafter, also referred to as a transcription repression converting peptide). The transcriptional repression converting peptide is not particularly limited as long as it is a peptide which is capable of inhibiting the function of the transcription factor by forming a chimeric protein fused with a transcription factor. Examples of such a transcription repression converting peptide include AtERF3 protein derived from *Arabidopsis thaliana* or a partial peptide thereof, AtERF4 protein derived from *Arabidopsis thaliana* or a partial peptide thereof, AtERF7 protein derived from *Arabidopsis thaliana* or a partial peptide, AtERF8 protein derived from *Arabidopsis thaliana* or a partial peptide thereof, AtERF8 protein derived from *Arabidopsis thaliana* or a partial peptide thereof (JP-A-2001-269177, JP-A-2001-269178, JP-A-2001-292776, and JP-A-2001-292777); ERF3 protein derived from tobacco or a partial peptide thereof (JP-A-2001-269176); and OsEFR3 protein derived from rice or a partial peptide thereof (JP-A-2001-269179), all of which belong to the Class II ERF gene family. Further examples also include ZAT10 protein derived from *Arabidopsis thaliana* or a partial peptide thereof, and ZAT11 protein derived from *Arabidopsis thaliana* or a partial peptide thereof, all of which belong to the gene family of zinc finger protein.

The various proteins described above have a motif containing aspartic acid-leucine-asparagine (DLN motif) in the carboxyl terminal region, and function as transcription repression converting peptides. The partial peptides of the various proteins contain the DLN motif.

Furthermore, SUPERMAN protein derived from *Arabidopsis thaliana* does not have the DLN motif, but is known to function as a transcription repression converting peptide, and the transcription repression function of the protein is very strong (The Plant Cell, Vol. 13, 1959-1968, August 2001; and FEBS Letters, 514, 351-354, 2002).

Further, examples of the transcription repression converting peptide include peptides having any of the amino acid sequences of SEQ ID NOS: 5 to 44. The transcription repression converting peptides can be isolated from the plant by methods well known to the skilled artisan, and can also be obtained by chemically synthesizing the peptides by methods well known to the skilled artisan.

The chimeric protein obtained by fusing a transcription factor involved in morphogenesis of floral organs of *cyclamen* and a transcription repression converting peptide, is not particularly limited in its constitution as long as the transcription factor and the transcription repression converting peptide are included therein, and any of the transcription factor and the transcription repression converting peptide may be located at the amino terminal side. Further, the chimeric protein may also contain a peptide having a linker function for linking the transcription factor with the transcription repression converting peptide, or various additional polypeptides such as polypeptides for epitope labeling the chimeric protein, such as His, Myc and Flag. In addition, if necessary, the chimeric protein may also contain a structure other than a polypeptide, for example, a sugar chain, an isoprenoid group or the like.

There are no particular limitations on the method of introducing into *cyclamen* a chimeric protein obtained by fusing a transcription factor involved in morphogenesis of floral organs of *cyclamen* and a transcription repression converting peptide, but it is preferable to introduce a DNA encoding the chimeric protein into *cyclamen*, to thereby produce the chimeric protein at floral organs of *cyclamen*.

A DNA encoding the chimeric protein (chimeric DNA) can be obtained by linking a DNA encoding a transcription factor involved in morphogenesis of floral organs of *cyclamen* with a DNA encoding a transcription repression converting peptide, so as to encode a fusion protein composed of the transcription factor and the transcription repression converting peptide.

A DNA encoding the transcription factor can be obtained by performing PCR by a conventional method using a primer pair prepared by a conventional method based on the nucleotide sequence of SEQ ID NO: 1, the nucleotide sequence of SEQ ID NO: 3, or the nucleotide sequence of the known transcription factor, and using the cDNA or genomic DNA of *cyclamen* as a template. Further, a DNA encoding the transcription factor can also be obtained by chemically synthesizing the DNA by a known method. Further, when a site-directed mutagenesis is introduced to the DNA obtained as such, a variant of the DNA, that is, a DNA which is hybridizable with the DNA under stringent conditions, can be obtained, and such a variant is also included in the DNA that encodes the transcription factor.

Further, a DNA encoding the transcription repression converting peptide can be obtained by performing PCR by a conventional method using a primer pair prepared by a conventional method based on the nucleotide sequence of a DNA encoding the known transcription repression converting peptide, and using the cDNA or genomic DNA of the plant from which the transcription repression converting peptide is derived as a template. Further, a DNA encoding the transcription repression converting peptide can also be obtained by chemically synthesizing the DNA by a known method.

The chimeric DNA can be obtained by chemically synthesizing a DNA having the nucleotide sequence of the desired chimeric DNA, by a method well known to the skilled artisan.

The chimeric DNA may include an additional nucleotide sequence for linking a DNA encoding a transcription factor involved in morphogenesis of floral organs of *cyclamen* with a DNA encoding a transcription repression converting peptide. Further, the chimeric DNA may also include an additional nucleotide sequence such as a nucleotide sequence for adjusting a triplet reading frame.

The method of introducing the chimeric DNA into *cyclamen* is not particularly limited, and any method capable of transforming *cyclamen* with the chimeric DNA can be employed. Among them, a method of transforming *cyclamen* with a recombinant expression vector into which the chimeric DNA has been inserted is preferred. A method of producing a recombinant expression vector, and a method of producing a *cyclamen* transformed with the expression vector are described below, but the present invention is not intended to be limited to these methods.

(a) Construction of Recombinant Expression Vector

A recombinant expression vector is a vector containing at least a promoter sequence, a nucleotide sequence encoding a transcription factor involved in morphogenesis of floral organs of *cyclamen*, and a nucleotide sequence encoding a transcription repression converting peptide.

As the vector which constitutes the base of the recombinant expression vector, various known vectors can be used. Examples of known vectors include plasmids, phages, cosmids and the like, and examples of plasmid vectors include pBR322, pBR325, pUC19, pUC119, pBluescript, pBluescriptSK, pBI vectors and the like. Among these vectors, a vector can be appropriately selected in accordance with the plant cell to be introduced and the transfection method. In the case of introducing a vector into *cyclamen* using *Agrobacterium*, it is preferable to use a pBI-based binary vector. Examples of the pBI-based binary vector include pBIG, pBIN19, pBI101, pBI121, pBI221 and the like.

The promoter is not particularly limited as long as it is a promoter capable of expressing, in the plant, a gene that is present in the downstream of the promoter. Examples of such a promoter include cauliflower mosaic virus 35S promoter (CaMV35S), an actin promoter, a nopaline synthetase promoter, a tobacco PR1a gene promoter, a tomato ribulose 1,5-diphosphate carboxylase/oxidase small subunit promoter and the like. Among them, cauliflower mosaic virus 35S promoter or an actin promoter is preferred. Further, a promoter which function in a floral organ-specific manner can also be suitably used.

In the recombinant expression vector, the promoter is linked so as to be able to express a chimeric DNA formed by linking a DNA encoding a transcription factor with a DNA encoding a transcription repression converting peptide. The recombinant expression vector may further contain other DNA segments in addition to the promoter and the chimeric DNA. There are no particular limitations on the other DNA segments. Examples of the DNA segments include a terminator, a selectable marker, an enhancer, and a DNA segment having a nucleotide sequence for increasing the translation efficiency.

Although the terminator is not particularly limited as long as it has a function as a transcription termination site, a transcription termination region for nopaline synthetase gene (Nos terminator), a transcription termination region for cauliflower mosaic virus 35S (CaMV35S terminator), and the like are preferred. Among those, a Nos terminator is preferred.

In the recombinant expression vector, when the terminator is disposed at an appropriate position, the phenomenon such that an unnecessarily long transcription product is synthesized after the recombinant expression vector is introduced into a plant cell, and a strong promoter reduces the plasmid copy number can be prevented.

As the selectable marker, for example, a drug resistance gene can be used. Examples of such a drug resistance gene include resistance genes against antibiotic agent such as hygromycin, bleomycin, kanamycin, gentamycin, and chloramphenicol. Thereby, when a *cyclamen* plant which has been subjected to a transformation treatment is cultured in a medium containing the antibiotic substances, a transformed cell or tissue can be easily selected by selecting the plant capable of growing in the medium.

Furthermore, the recombinant expression vector may further have a T-DNA region. A recombinant expression vector having a T-DNA region is preferred from the viewpoint that when the recombinant expression vector is introduced into *cyclamen* through *Agrobacterium*, the incorporation efficiency of the target gene into the genomic DNA of *cyclamen* can be enhanced.

There are no particular limitations on the method of constructing the recombinant expression vector, and a promoter, a DNA encoding a transcription factor involved in morphogenesis of floral organs of *cyclamen*, a DNA encoding a transcription repression converting peptide, and as necessary, the other DNA segments as described above may be inserted into a vector in a predetermined order. For example, a recombinant expression vector can be prepared by linking the DNA encoding a transcription factor with the DNA encoding a transcription repression converting peptide, thereby constructing a chimeric DNA, subsequently linking a promoter to the upstream of this chimeric DNA, linking a terminator, as necessary, to the downstream of the chimeric DNA, thereby constructing a so-called expression cassette, and introducing this expression cassette into a basic vector.

In the construction of a chimeric DNA and the construction of an expression cassette, for example, the terminals of the various DNA elements such as a gene, a promoter, and a terminator can converted to cohesive ends that are complementary to each other, by using a restriction enzyme, and the various DNA elements can be linked in a predetermined order by causing a ligation enzyme to act. As the restriction enzyme, the ligation enzyme, and the like, commercially available enzymes may be appropriately selected and used.

The recombinant expression vector thus prepared can be replicated by introducing it into a host cell such as *Escherichia*, and allow the host cell to proliferate. The recombinant expression vector can be recovered from the proliferated host cells by a known method.

(b) Transformation

A *cyclamen* plant can be transformed with the recombinant expression vector described above, and thus the chimeric DNA expression cassette can be introduced into the cell.

Examples of the *cyclamen* plant that is transformed include the tissues and cells constituting organs such as flowers, leaves, and roots of *cyclamen*, as well as the callus, adventitious embryo, and suspension cultured cells.

There are no particular limitations on the method of introducing the recombinant expression vector into a *cyclamen* plant, and any known method can be used. For example, a method of infecting the tissues, cells, and the like of *cyclamen* with an *Agrobacterium* that retains the recombinant expression vector, to thereby insert an expression cassette of a chimeric protein into the genome of the cells transfected with *Agrobacterium*; or a method of directly introducing a recombinant expression vector into the cells of *cyclamen*, such as a microinjection method, an electroporation method (electric perforation method), a polyethylene glycol method, a particle gun method, a protoplast fusion method, or a calcium phosphate method, can be used.

(c) Selection and Regeneration of Transformed Plant

The method of selecting a transformant is not particularly limited. The selection may be made by using, as an indicator, the resistance to a drug such as hygromycin or kanamycin of the plants which were subjected to the transformation treatment, or the selection may be made by using, as an indicator, the flower morphology of a *cyclamen* grown by regenerating the plants which were subjected to the transformation treatment.

As an example of selecting the transformant based on the flower morphology, a method of comparing the flower morphology of *cyclamens* grown by regenerating the plants which were subjected to the transformation treatment with the flower morphology of a *cyclamen* which has not been transformed, and selecting among the *cyclamens* derived from the plants which were subjected to the transformation treatment, a *cyclamen* having an increased number of petals as compared to the *cyclamen* which has not been subjected to the transformation treatment, may be employed. The method of selecting by using the flower morphology as an indicator is preferred from the viewpoint that the selection can be achieved only by simply making a comparison through visual inspection, and the effects of the present invention including a modification of the morphology of the floral organs, particularly an increased number of petals, can be verified per se.

As the method of regenerating a plant such as a cell, that has been transformed (hereinafter, may be referred to as a transformed plant), and growing a *cyclamen* having petals, any known method can be used, and thereby a multi-petaled *cyclamen* plant having an increased number of petals can be obtained.

The production method of the present invention may include subjecting a transformed plant to a regeneration treatment, thereby obtaining a *cyclamen* that has been grown from the transformed plant, and obtaining a descendant having modified flower morphology from the obtained *cyclamen* through sexual reproduction or asexual reproduction. Furthermore, the production method may also include obtaining plant cells, or breeding materials such as seeds, fruits, stumps, calluses, tubers, scions, and clusters from a *cyclamen* that has been regenerated from transformed cells, or from a descendant thereof; regenerating these; and thereby obtaining again a grown *cyclamen* having petals. Namely, the production method of the present invention may include propagating a transformed plant (step of mass production).

Confirmation of the incorporation of a desired chimeric DNA into a transformed plant can be achieved by extracting the DNA according to a routine method from the plant or from the tissues of a *cyclamen* regenerated from the plant, and performing a conventional method such as a polymerase chain reaction (PCR) method or a Southern hybridization method.

In the present invention, the term "the number of petals has increased" means that the number of petals has increased as compared to a *cyclamen* that has not been transformed. There are no particular limitations on the mode in which the number of petals has increased, but an example may be a mode in which a stamen or a pistil has been modified into the form of petal.

Meanwhile, the term "*cyclamen* plant" as used in the present invention means a plant that belongs to the genus *Cyclamen*. Furthermore, in the present invention, the term "plant" is used as a concept encompassing a grown individual plant, plant cells, plant tissues, plant organs, calluses, seeds, and the like. The plant cells include plant cells of various forms. Examples of such plant cells include suspension cultured cells, protoplasts, and leaf sections.

Hereinafter, the present invention is specifically described by way of Examples, but the scope of the present invention is not intended to be limited thereto. Unless particularly stated, the following experimental procedure follows the method described in "Molecular Cloning, 2nd Edition" (J. Sambrook, et al., Cold Spring Harbor Laboratory press, 1989).

EXAMPLES

Reference Example 1

Isolation of *Cyclamen*-Derived Transcription Factor AGAMOUS (1) Preparation of *Cyclamen* Bud-Derived Total RNA Was 0.1 g of buds (sepals, petals, androphores and gynaeceums) of a *cyclamen* (variety: Fragrance Mini) frozen in the presence of liquid nitrogen, and then the frozen buds were crushed using a crusher, MM300 (manufactured by QIAGEN N.V.). Was 0.75 ml of a 2×CTAB solution (0.1 M Tris-HCl (pH 9.5), 20 mM EDTA, 1.4 M NaCl, 4% β-mercaptoethanol, and 2% cetyltrimethylammonium bromide) added to the crushed product, and the mixture was stirred and incubated for 10 minutes at 65° C. Subsequently, the operation of chloroform extraction was carried out twice, and thus nucleic acid was collected. To the nucleic acid extract thus obtained, an equal amount of isopropanol was added, and the mixture was centrifuged for 10 minutes at 21,000 g at 4° C. to precipitate the nucleic acid. This precipitate was dissolved in 0.8 ml of TE (10 mM Tris-HCl (pH 8.0), and 1 mM EDTA). Was 0.2 ml of a 10 M lithium chloride solution added to the solution, and the mixture was left to stand for 2 hours on ice. Subsequently, the mixture was centrifuged for 10 minutes at 21,000 g at 4° C., and thereby the total RNA was precipitated. The precipitated total RNA was dissolved in distilled water, and then phenol/chloroform extraction was carried out. A nucleic acid fraction thus obtained was subjected to an ethanol precipitation operation, and thereby the total RNA was purified. The precipitated total RNA was dissolved in an appropriate amount of TE, and the concentration was measured with a spectrophotometer. The yield was 11.5 µg. In order to use the solution in the subsequent experiments, the concentration of the RNA solution was adjusted to 1 mg/ml.

(2) Cloning of cDNA Fragment Located in 3'-Terminal Side Region of Gene Encoding Transcription Factor AGAMOUS of *Cyclamen*

(i) In order to clone a cDNA fragment of a gene encoding transcription factor AGAMOUS (hereinafter, referred to as AG) of *cyclamen* using the 3' RACE method, a degenerate primer was designed based on the alignment of the AG genes of *Arabidopsis thaliana*, gerbera, petunia and rose. An oligonucleotide having the nucleotide sequence of SEQ ID NO: 45 and an oligonucleotide having the nucleotide sequence of SEQ ID NO: 46 (wherein K in the nucleotide sequences represents G or T; Y represents T or C; M represents A or C; and R represents A or G) were designed as a primer for 1st PCR and a primer for Nested PCR, respectively, and the oligonucleotides were prepared by using a custom DNA synthesis service (Hokkaido System Science Co., Ltd.). Hereinafter, the preparation of oligonucleotides was carried out using the custom DNA synthesis service (Hokkaido System Science Co., Ltd.).

(ii) A reverse transcription reaction was carried out by the 3' RACE System for Rapid Amplification of cDNA Ends (manufactured by Invitrogen Corp.) using 1 μg of the total RNA obtained in the above section (1) as a template, and using the reaction product as a template, PCR was performed after adding the primer for 1st PCR to be a final concentration of 0.3 μM. Subsequently, Nested PCR was performed using the PCR amplification product as a template, after adding the primer for Nested PCR to be a final concentration of 0.3 μM. Thus, the amplification of a cDNA fragment which located in the 3'-terminal region of *cyclamen* AG gene was carried out. As the PCR reaction apparatus, an iCycler Thermal Cycler manufactured by Bio-Rad Laboratories, Ltd. was used. Takara LATaq (manufactured by Takara Bio, Inc.) was used as the DNA polymerase, and the amplification reaction liquid was prepared using the reagents supplied therewith. The PCR was carried out by performing a denaturation reaction for 2 minutes at 95° C., and subsequently performing 30 cycles of a reaction consisting of three steps, including a denaturation reaction for 30 seconds at 94° C., an annealing reaction for 1 minute at 52° C., and an extension reaction for 1 minute at 72° C.

Was 5 μl of the reaction liquid obtained after the Nested PCR subjected to electrophoresis, and it was confirmed that a DNA having a size assumed to be obtainable from the designed primers had been amplified.

(iii) The amplification product of the Nested PCR was linked to the TA site of a TA vector, pT7Blue Vector (manufactured by Navagen Inc.). *Escherichia coli* DH5α was transformed with the linked vector thus obtained, and thereby a transformed *E. coli* retaining the DNA fragment, which was the amplification product, was obtained.

Plural cells of the transformed *E. coli* were selected and proliferated, and a plasmid DNA was extracted therefrom using the Wizard Plus SV Minipreps DNA Purification Systems (manufactured by Promega Corp.). In the following experiments, Wizard Plus SV Minipreps DNA Purification Systems (manufactured by Promega Corp.) was used in the extraction of plasmid DNAs. The plasmid DNA (vector) was treated with a restriction enzyme corresponding to the restriction enzyme site presented in the multicloning site of the plasmid DNA, and then this treated plasmid DNA was electrophoresed. Thereby, it was confirmed that the target amplification product had been inserted into the plasmid DNA. Subsequently, the nucleotide sequence of the amplification product was determined by using a custom DNA sequencing service (FASMAC Co., Ltd.). In the following experiments, the determination of nucleotide sequences was carried out using a custom DNA sequencing service (FASMAC Co., Ltd.).

As a result, it was confirmed that the amplification product contained a 826-bp nucleotide sequence which included the poly(A) signal. A comparison was made between the nucleotide sequence thus determined and the nucleotide sequence of the AG gene family that has been found so far, and as a result, it was strongly suggested that the amplification product was a DNA fragment encoding the 3'-terminal side region of *cyclamen*-derived AG gene. Thus, the DNA fragment was named CpAG3'.

(3) Cloning of cDNA Fragment Located in 5'-Terminal Side Region of Gene Encoding Transcription Factor AGAMOUS of *Cyclamen*

(i) A primer for the use in cloning of the upstream region in the gene including CpAG3' was designed by using the 5' RACE method. An oligonucleotide having the nucleotide sequence of SEQ ID NO: 47 (wherein K in the nucleotide sequences represents G or T; Y represents T or C; M represents A or C; and R represents A or G), and an oligonucleotide having the nucleotide sequence of SEQ ID NO: 48, which had been designed based on the nucleotide sequence of CpAG3', were prepared as a primer for 1st PCR and a primer for Nested PCR, respectively.

(ii) A reverse transcription reaction was carried out by the 5' RACE System for Rapid Amplification of cDNA Ends (manufactured by Invitrogen Corp.) using 1 μg of the total RNA obtained in the above section (1) as a template, and then, using the reaction product as a template, PCR was performed after adding the primer for 1st PCR to be a final concentration of 0.3 μM. Subsequently, Nested PCR was performed using the PCR amplification product as a template, after adding the primer for Nested PCR to be a final concentration of 0.2 μM. Thus, the amplification of a cDNA fragment which located in the 5'-terminal side region of *cyclamen* AG gene was carried out. The PCR was carried out under the same conditions as those used in the section (2)(ii).

Was 5 μl of the reaction liquid obtained after the Nested PCR electrophoresed, and it was confirmed that a DNA having a size assumed to be obtainable from the designed primers had been amplified.

(iii) The amplification product of the Nested PCR was linked to the TA site of a TA vector, pT7Blue Vector (manufactured by Navagen, Inc.). *Escherichia coli* DH5α was transformed with the linked vector thus obtained, and thereby a transformed *E. coli* retaining the DNA fragment, which was the amplification product, was obtained.

Plural cells of the transformed *E. coli* were selected and proliferated, and a plasmid DNA was extracted therefrom. The plasmid DNA (vector) was treated with a restriction enzyme corresponding to the restriction enzyme site present in the multicloning site of the plasmid DNA, and then this treated plasmid DNA was electrophoresed. Thereby, it was confirmed that the target amplification product had been inserted into the plasmid DNA. Subsequently, the nucleotide sequence of the amplification product was determined.

As a result, two DNA fragments, respectively having a 538-bp nucleotide sequence and a 482-bp nucleotide sequence, which were believed to encode the upstream region of the 5'-terminal side of *cyclamen* AG gene, were confirmed. These DNA fragments were named CpAG5'-1 and CpAG5'-2, respectively.

(4) Nucleotide Sequence Analysis of CpAG3', CpAG5'-1 and CpAG5'-2

In order to analyze the nucleotide sequences of CpAG3', CpAG5'-1 and CpAG5'-2 determined in the sections (2) and (3), a nucleotide sequence alignment file was prepared using the software Genetyx (manufactured by Genetyx Corp.) under the default conditions of the software. As a result, CpAG5'-1 and CpAG5'-2 had a 93% identity of the nucleotide sequence. Furthermore, the nucleotide sequence of CpAG3' gene was partially identical with the nucleotide sequence of CpAG5'-1 gene, and thus the nucleotide sequences were combined. It was found that the nucleotide sequences constitute a gene having one open reading frame (ORF). This gene having a single ORF was named CpAG1 gene. This CpAG1 gene has a DNA sequence having a full length of 1083 nucleotides and an ORF containing 741 nucleotides. Furthermore, a gene containing CpAG5'-2 was named CpAG2 gene.

In addition, the restriction enzyme maps of CpAG1 gene and CpAG5'-2 were prepared using Genetyx, and a comparison thereof was made. It was found that CpAG5'-2 contained a SpeI site which does not exist in the CpAG1 gene.

(5) Cloning of CpAG1 Gene

For the purpose of cloning the ORFs of the CpAG1 gene and the CpAG2 gene, an oligonucleotide having the nucleotide sequence of SEQ ID NO: 49 and an oligonucleotide having the nucleotide sequence of SEQ ID NO: 50 were prepared as a forward primer and a reverse primer, respectively.

Subsequently, 20 µl of a reverse transcription reaction liquid was prepared using a reverse transcriptase, that is, PrimeScript Reverse Transcriptase (manufactured by Takara Bio, Inc.), 1 µl of oligo(dT), that is, 12-18 primer (manufactured by Invitrogen Corp.) and the reagents supplied together with the reverse transcriptase, and a reverse transcription reaction was carried out using 1 µg of the total RNA obtained in the section (1) as a template. The reverse transcription reaction was carried out by sequentially incubating the reverse transcription reaction liquid for 10 minutes at 30° C.; for 30 minutes at 50° C.; for 5 minutes at 99° C.; and for 5 minutes at 4° C.

Subsequently, a reaction liquid for PCR amplification containing 1 µl of the reaction liquid obtained after the reverse transcription reaction was prepared, and the forward primer and the reverse primer were respectively added thereto to be a final concentration of 0.3 µM for each of the primers. PCR was carried out using KODPlus (manufactured by Toyobo Co., Ltd.) as a DNA polymerase. The amplification reaction liquid used herein was prepared by using the reagents supplied together with KODplus (manufactured by Toyobo Co., Ltd.). As the PCR reaction apparatus, an iCycler Thermal Cycler manufactured by Bio-Rad Laboratories, Ltd. was used. The PCR was carried out by performing a denaturation reaction for 2 minutes at 95° C., and subsequently performing 30 cycles of three reactions including a denaturation reaction for 30 seconds at 94° C., an annealing reaction for 1 minute at 58° C., and an extension reaction for 1 minute at 68° C. Was 5 µl of the reaction liquid thus obtained after the PCR electrophoresed, and it was confirmed that a DNA having a size assumed to be obtainable from the designed primers had been amplified.

(iii) The amplification reaction product was subjected to a phosphorylation treatment, and then an operation of linking the amplification product to the SmaI site of pBlueScript II SK(−) (manufactured by Stratagene Corp.) was carried out. E. coli DH5α was transformed with the linked vector thus obtained, and thereby a transformed E. coli retaining the amplification product DNA fragment was obtained.

Plural cells of the transformed E. coli were selected and proliferated, and a plasmid DNA was extracted therefrom. The plasmid DNA (vector) was treated with a restriction enzyme corresponding to the restriction enzyme site present in the multicloning site of the plasmid DNA and with SpeI, and then this treated plasmid DNA was electrophoresed. Thereby, it was confirmed that the target amplification product had been inserted into the plasmid DNA. However, a clone having the SpeI site was not obtained.

Furthermore, four clones of the transformed E. coli were selected, and a nucleotide sequence analysis of their amplification product DNA fragments was carried out. As a result, all of the four clones had the ORF of CpAG1 gene.

The CpAG1 gene could be cloned by the method described above, but the CpAG2 gene could not be cloned. One of the reasons that can be speculated is that the sequence of the non-translated region of the 3'-terminus side of the CpAG2 gene is significantly different from that of the CpAG1 gene.

(6) Cloning of CpAG2 Gene (i) In order to clone the 3'-terminal region of the CpAG2 gene, a portion having a low sequence identity was selected from the alignment of the nucleotide sequence of the CpAG1 gene and the nucleotide sequence of CpAG5'-2 prepared in the section (4), and two oligonucleotides having the nucleotide sequences of SEQ ID NO: 51 and SEQ ID NO: 52 were produced as primers.

The 3' RACE was carried out in the same manner as in the section (2), using the two primers described above, and the nucleotide sequence of the amplification product thus cloned was determined. As a result, it was confirmed that the cloned DNA fragment was a cDNA having a 698-bp nucleotide sequence including the poly(A) signal.

(ii) Furthermore, the 5' RACE was carried out in order to verify whether the full length of the 5'-terminal region of the CpAG2 gene had been cloned. A comparison was made between the CpAG1 gene and the nucleotide sequence determined in the section (6)(i), and thus an oligonucleotide having a nucleotide sequence having a low identity (SEQ ID NO: 53) was prepared as a primer for 1st PCR. Further, an oligonucleotide having the nucleotide sequence of SEQ ID NO: 48 was produced as a Nested primer.

The 5' RACE was carried out in the same manner as in the section (3), and the nucleotide sequence of the cloned amplification product was determined. As a result, it was confirmed that the cloned DNA fragment was a cDNA having a 517-bp nucleotide sequence.

(iii) The nucleotide sequences obtained by 3' RACE and 5' RACE were aligned, and thereby it was found that there was a cDNA containing 1073 nucleotides and containing one ORF. Thereafter, the CpAG2 gene was cloned by the same method as that used in the section (5).

(7) Nucleotide Sequence Analysis of CpAG1 and CpAG2 Genes

The nucleotide sequences of the ORF of the CpAG1 gene and the CpAG2 gene shared a 90% identity, and the deduced amino acid sequences also shared a 90% identity. The deduced amino acid sequences were compared with the amino acid sequence of AG gene that is already known, and the amino acid sequences exhibited high identity. Thus, it was speculated that the CpAG1 gene and the CpAG2 gene are orthologous genes of the transcription factor AG.

CpAG1 gene of *cyclamen* has a 1083-bp nucleotide sequence (SEQ ID NO: 1), and the sequence includes therein a 741-bp nucleotide sequence which is a single open reading frame (a nucleotide sequence extending from Nucleotide Number 111 to Nucleotide Number. 851 of SEQ ID NO: 1).

This open reading frame encodes a protein having the sequence of SEQ ID NO: 2 containing 247 amino acid residues.

CpAG2 gene of *cyclamen* has a 1073-bp nucleotide sequence (SEQ ID NO: 3), and the sequence includes therein a 744-bp nucleotide sequence which is a single open reading frame (a nucleotide sequence extending from Nucleotide Number 87 to Nucleotide No. 830 of SEQ ID NO: 3). This open reading frame encodes a protein having the sequence of SEQ ID NO: 4 containing 248 amino acid residues.

The cDNAs of CpAG1 gene and CpAG2 gene have been subcloned into a Bluescript plasmid vector, and the *Escherichia coli* transfected with this plasmid vectors were named *Escherichia coli* DH5α (CpAG-1, CpAG-2) and were deposited with the International Patent Organism Depositary at the National Institute of Advanced Industrial Science and Technology, on Nov. 5, 2010, under the Accession Nos. FERM BP-11306 and FERM BP-11307.

Reference Example 2

Construction of Vector for Transformation (1) Preparation of Vector p35SG for Constructing Vector for Transformation
(i) The region of attL1 on a pENTR vector (manufactured by Invitrogen Corp.) was amplified by PCR using two primers, attL1-F (SEQ ID NO: 54) and attL1-R (SEQ ID NO: 55), and the attL1 fragment thus obtained was digested with restriction enzyme HindIII, followed by purification. Furthermore, the region of attL2 was amplified by PCR using two primers, attL2-F (SEQ ID NO: 56) and attL2-R (SEQ ID NO: 57). The attL2 fragment thus obtained was digested with EcoRI and purified. The PCR was carried out such that one cycle of denaturation for 1 minute at 94° C., an annealing reaction for 2 minutes at 47° C., and an extension reaction for 1 minute at 74° C. was performed 25 times. In the following experiments, all PCR reactions were carried out under the same conditions.
(ii) Plasmid pBI221 (manufactured by Clontech Laboratories, Inc., USA) was excised with restriction enzymes XbaI and SacI, and then β-glucuronidase (GUS) gene was removed by agarose gel electrophoresis. Thus, a 35S-Nos plasmid fragment DNA containing the cauliflower mosaic virus 35S promoter (hereinafter, may be referred to as CaMV35S) and the transcription termination region of nopaline synthetase gene (hereinafter, may be referred to as Nos-ter) was obtained.
(iii) A DNA fragment having the nucleotide sequence of SEQ ID NO: 58, and a DNA fragment having the sequence of SEQ ID NO: 59 were synthesized, and the DNA fragments were heated for 2 minutes at 90° C. and then heated for 1 hour at 60° C. Subsequently, the DNA fragments were annealed by leaving them to stand for 2 hours at room temperature (25° C.), and thus a double-stranded chain was formed. This was ligated into the XbaI-SacI region of the $^{35}$S-Nos plasmid fragment DNA, and thus the p35S-Nos plasmid was completed. The DNA fragment having the sequences of SEQ ID NO: 58 and SEQ ID NO: 59 contains, from the 5'-terminus, a BamHI restriction enzyme site, the tobacco mosaic virus-derived omega sequence for increasing the translation efficiency, and restriction enzyme sites SmaI, SalI and SstI, in this order.
(iv) This p35S-Nos plasmid was digested with restriction enzyme HindIII, and the attL1 fragment was inserted therein. Furthermore, this was digested with EcoRI, the attL2 fragment was inserted, and thus vector p35SG was completed.

(2) Construction of Vector p35SSRDXG Incorporated with DNA Encoding Transcription Repression Converting Peptide
(i) A polynucleotide (SEQ ID NO: 60) that was designed to encode a transcription repression converting peptide (SRDX) having the amino acid sequence of SEQ ID NO: 21, and to have the termination codon TAA at the 3'-terminus, and a complementary strand thereof (SEQ ID NO: 61) were synthesized. The nucleotides were heated for 10 minutes at 70° C., and then were annealed by natural cooling to obtain a double-stranded DNA.
(ii) The vector p35SG was digested with restriction enzymes SmaI and SalI, and the double-stranded DNA that encodes the SRDX was inserted into this region. Thus, vector p35SSRDXG was constructed.
(3) Incorporation of CpAG1 Gene into Vector p35SSRDXG
(i) From the CpAG1 gene obtained in Test Example 1, a DNA fragment containing only the coding region for *cyclamen* CpAG1 gene except for the termination codon, was amplified by PCR using an oligonucleotide having the nucleotide sequence of SEQ ID NO: 62 and an oligonucleotide having the nucleotide sequence of SEQ ID NO: 63 as a primer set.
(ii) The DNA fragment of the coding region of CpAG1 gene thus obtained was ligated to the SmaI site of the vector p35SSRDXG that had been digested in advance with restriction enzyme SmaI.
(iii) *Escherichia coli* was transformed with this plasmid, the plasmid was thus prepared, and the nucleotide sequence was determined. A clone having the insert in the forward direction was isolated, and thereby vector p35SCpAG1SRDXG in which a chimeric gene obtained by fusing CpAG1 gene and a gene encoding SRDX had been incorporated, was obtained.
(4) Incorporation of CpAG2 Gene into Vector p35SSRDXG
(i) From the CpAG2 gene obtained from Test Example 1, a DNA fragment containing only the coding region for *cyclamen* CpAG2 gene except for the termination codon was amplified by PCR using an oligonucleotide having the nucleotide sequence of SEQ ID NO: 62 and an oligonucleotide having the nucleotide sequence of SEQ ID NO: 64 as a primer set.
(ii) The DNA fragment of the coding region of CpAG2 gene thus obtained was ligated to the SmaI site of the vector for construction, p35SSRDXG, which had been digested in advance with restriction enzyme SmaI.
(iii) *Escherichia coli* was transformed with this plasmid, the plasmid was thus prepared, and the nucleotide sequence was determined. A clone having the insert in the forward direction was isolated, and thereby vector p35SCpAG2SRDXG in which a chimeric gene obtained by fusing CpAG2 gene and a gene encoding SRDX had been incorporated, was obtained.
(5) Construction of Vector Retaining 35SCpAG1SRDXG and CpAG2SRDXG
Vector p35SCpAG1SRDXG:35 SCpAG2SRDXG, which simultaneously retained the DNA fragments of 35SCpAG1SRDXG and 35SCpAG2SRDXG, was constructed by utilizing the vectors p35SCpAG1SRDXG and p35SCpAG2SRDXG prepared in the sections (3) and (4).
(6) Construction of Recombinant Expression Vector
A DNA fragment containing the CaMV35S promoter, the chimeric gene, the Nos-ter and the like on the vector prepared in the sections (3), (4) and (5), was recombined into a vector for plant transformation, pBIGCKH (obtained from the National Institute of Advanced Industrial Science and Technology), and thereby an expression vector which uses a plant as a host was constructed. Specifically, the construction was carried out according to the following steps (i) to (iii) using Gateway (registered trademark) LR clonase (registered trademark, manufactured by Invitrogen Corp.).

(i) Was 4.0 µL (about 600 ng) of pBIGCKH mixed separately with 1.5 µL (about 300 ng) of p35SCpAG1SRDXG, with 1.5 µL (about 300 ng) of p35SCpAG2SRDXG, or with 1.5 µL (about 300 ng) of p35SCpAG1SRDXG:35SCpAG2SRDXG, and to each of the mixtures, 4.0 µL of LR buffer that had been diluted 5 times, and 5.5 mL of a TE buffer solution (10 mM Tris-HCl (pH 7.0), 1 mM EDTA) were added.

(ii) Was 4.0 µL of LR clonase added to these solutions, and the mixtures were incubated for 60 minutes at 25° C. Subsequently, 2 µL of proteinase K was added thereto, and the resulting mixtures were incubated for 10 minutes at 37° C.

(iii) Was 1 to 2 µL of each of these solutions separately introduced into *Escherichia coli* (DH5α or the like), and transformed *E. coli* cells were selected by using hygromycin resistance as an indicator.

Thereby, vectors for plant transformation, p35 CpAG1SRDX, p35 CpAG2SRDX, and p35SCpAG1SRDX: 35SCpAG2SRDX, were obtained.

(7) Transformation of *Agrobacterium* with Vectors for Plant Transformation

From the respective *E. coli* cells having the vectors for plant transformation, p35 CpAG1SRDX or p35 CpAG2SRDX, the vectors were respectively extracted as plasmid DNAs, and each of the vectors was introduced into *Agrobacterium tumefaciens* (EHA101) and *Agrobacterium tumefaciens* (LBA4404) by an electroporation method. Furthermore, p35 CpAG1SRDX:35 CpAG2SRDX was introduced into *Agrobacterium tumefaciens* (LBA4404) by an electroporation method. The bacteria were stationary cultured for 2 days at 28° C. on LB medium containing hygromycin, and thus *Agrobacterium tumefaciens* (EHA101) retaining the vector for plant transformation, p35 CpAG1SRDX; *Agrobacterium tumefaciens* (LBA4404) retaining the vector for plant transformation, p35 CpAG2SRDX; and *Agrobacterium tumefaciens* (LBA4404) retaining the vector for plant transformation, p35 CpAG1SRDX:35 CpAG2SRDX were obtained.

Example

Introduction of Chimeric Gene into *Cyclamen*

(1) Introduction into Single-Flowered Variety

Seeds of *cyclamen* (variety: Melody White) were immersed for 20 minutes in a sodium hypochlorite solution having an effective chlorine concentration of 1% for sterilization. Subsequently, the seeds were bedded in a medium (pH 5.8) prepared by adding, to MS medium at half the inorganic salt concentration, sucrose to be a final concentration of 3% and gellan gum to be a final concentration of 0.3%, and were cultivated for 60 days at 20° C. in the dark. The petiole parts of the seedlings produced as the seeds germinated were cut to a length of 5 mm to be used as tissue sections for gene introduction. One hundred tissue sections per experimental plot were bedded in a solid medium which was prepared by adding, to MS medium at half the inorganic salt concentration, sucrose to be a final concentration of 3%, thidiazuron as a plant hormone to be a final concentration of 1 mg/L, 2,4-D to be a final concentration of 1 mg/L, and acetosyringone to be a final concentration of 20 mg/L, adjusting the medium to pH 5.8, and then adding Gelrite to be a final concentration of 0.3%. The container used in this cultivation was a sterilized plastic Petri dish (diameter 9 cm, height 1.5 cm), and ten tissue sections were bedded per Petri dish. This was cultivated for 7 days at 20° C. in the dark.

*Agrobacterium tumefaciens* (EHA101) having the recombinant vector p35SCpAG1SRDX described above was cultured overnight in LB medium at 28° C. *Agrobacterium* cells were collected from the culture fluid by centrifugation, and then the cells were suspended in 10 mL of a liquid medium prepared by adding 3% of sucrose to the MS medium at one-third of the inorganic salt composition, to obtain a bacterial fluid. One hundred tissue sections obtained after the cultivation of *cyclamen* petioles were immersion treated for 30 minutes. After the immersion treatment, the *cyclamen* petioles were bedded in a solid medium which was prepared by adding, to MS medium at half the inorganic salt concentration, sucrose to be a final concentration of 3%, thidiazuron as a plant hormone to be a final concentration of 1 mg/L, 2,4-D to be a final concentration of 1 mg/L, and acetosyringone to be a final concentration of 20 mg/L, adjusting the medium to pH 5.8, and then adding Gelrite to be a final concentration of 0.3%. The tissue sections were co-cultivated for 6 days in the dark under the temperature conditions of 20° C.

The one hundred tissue sections obtained after the co-cultivation were transferred to a 50-mL sterile centrifuge tube (inner diameter 27 mm, length 115 mm), and were washed by adding 30 mL of a washing liquid (a liquid prepared by adding carbenicillin to be a final concentration of 300 mg/L to MS liquid medium at half the inorganic salt concentration). Furthermore, this operation was repeated six times, and then excess water was removed using sterile filter paper. The washed tissue sections were bedded in a callus proliferation medium prepared by adding, to MS medium at half the inorganic salt concentration, sucrose to be a final concentration of 3%, thidiazuron as a plant hormone to be a final concentration of 1 mg/L, 2,4-D to be a final concentration of 1 mg/L, carbenicillin to be a final concentration of 500 mg/L, and hygromycin to be a final concentration of 5 mg/L, adjusting the medium to pH 5.8, and adding Gelrite to be a final concentration of 0.3%. The tissue sections were transplanted into fresh selection medium every one month in the dark at 20° C.

(2) Introduction into Double-Flowered Mutant Variety

The processes were carried out by the same method as that used in the section (1), except that leaf blades of *cyclamen* (variety: Wink Pink) were used as the tissues for gene introduction, and to infect *Agrobacterium tumefaciens* (LAB4404) containing recombinant vector p35SCpAG2SRDX.

Furthermore, the expression of CpAG1 and CpAG2 in the Wink Pink variety was confirmed by RT-PCR, and only the expression of CpAG2 was confirmed, while the expression of CpAG1 was not recognized. That is, the Wink Pink variety was a double-flowered mutant variety which had lost the function of CpAG1 gene.

(3) Production of Transformed *Cyclamen*-1

The tissue sections transplanted to the selection medium in the sections (1) and (2) formed hygromycin-resistant transformed calluses in about two months. These calluses were bedded in an adventitious bud regeneration medium which was prepared by adding, to MS medium at one-third of the inorganic salt concentration, sucrose to be a final concentration of 3%, NAA as a plant hormone to be a final concentration of 0.2 mg/L, BA to be a final concentration of 0.02 mg/L, carbenicillin to be a final concentration of 300 mg/L, and hygromycin to be a final concentration of 5 mg/L, adjusting the medium to pH 5.8, and then adding Gelrite to be a final concentration of 0.3%. The calluses were transplanted into a fresh adventitious bud regeneration medium every month in the dark at 20° C.

After the transplantation to a regeneration medium, adventitious buds were formed from the transformed calluses in about two months. These adventitious buds were cut out, and were bedded in a rooting medium which was prepared by adding, to MS medium at one-third of the inorganic concentration, sucrose to be a final concentration of 3% and NAA as a plant hormone to be a final concentration of 0.1 mg/L, adjusting the medium to pH 5.8, and then adding Gelrite to be a final concentration of 0.3%. The adventitious buds were cultivated in the light (illuminated at 1000 lux for 16 hours) at 20° C. As a result, eight *cyclamen* plant bodies (Melody White transformants) grown from the tissue sections that had been transformed with CpAG1SRDX, and twelve *cyclamen* plant bodies (Wink Pink transformants) grown from the tissue sections that had been transformed with CpAG2SRDX were obtained.

(4) Evaluation of Cultivation of Transformed *Cyclamen*-1

With regard to the transformed *cyclamen* obtained in the section (3), the leaves were used as a material for genetic analysis, and it was confirmed by PCR that a fusion gene of CpAG1 gene or CpAG2 gene and a gene encoding SRDX had been introduced.

The results of a comparison made between the phenotype of Melody White, a single-flowered variety, which had been transformed with CpAG1SRDX, and the phenotype of Melody White that had not been transformed, are presented in FIG. 1. As is obvious from FIG. 1, the Melody White transformed with CpAG1SRDX had an increased number of petals as compared to the Melody White that had not been transformed, and it could also be confirmed that stamens had been converted to petals.

Figure 2:
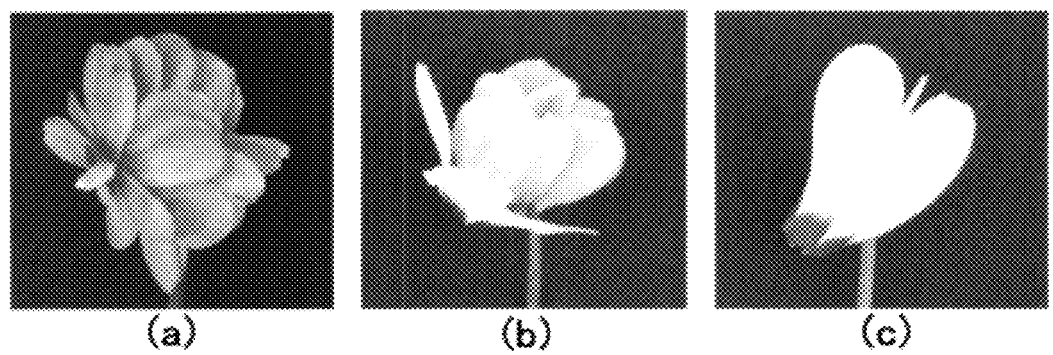
FIG. 2 illustrates the photographs of (a) the floral organs of a Wink Pink which has been transformed with CpAG2SRDX; (b) the floral organs of a Wink Pink which has not been transformed; and (c) the floral organs of wild type *cyclamen*.

Furthermore, the results of a comparison made between the phenotype of Wink Pink, a double-flowered mutant variety, which had been transformed with CpAG2SRDX, and the phenotype of Wink Pink that had not been transformed, are presented in FIG. 2. As is obvious from FIG. 2, in the Wink Pink transformed with CpAG2SRDX, stamens and pistils had been converted to petals, and the number of petals markedly increased as compared to the Wink Pink that had not been transformed. Further, when compared to wild type *cyclamen*, it was found that the increase in the number of petals is very conspicuous.

(5) Introduction of Two Chimeric Genes into Single-Flowered Variety

Tissue sections for gene transduction of *cyclamen* (variety: Fragrance Mini Amethyst Blue) were prepared by the same method as that used in the section (1). One hundred tissue sections per experimental plot were bedded in a solid medium containing sucrose at 5%, 2,4-D at 4 mg/L, kinetin at 0.1 mg/L, acetosyringone at 20 mg/L, and Gelrite at 0.3%. The container used in this cultivation was a sterilized plastic Petri dish (diameter 9 cm, height 1.5 cm), and ten tissue sections were bedded in one Petri dish. This was cultivated for 7 days at 20° C. in the dark.

The *Agrobacterium tumefaciens* (LAB4404) retaining p35SCpAG1SRDX:35SCpAG2SRDX as described above was cultured in LB liquid medium for 12 hours at 28° C. The *Agrobacterium* cells were collected from the culture fluid by centrifugation, and then were suspended in 10 mL of a liquid medium prepared by adding 3% of sucrose to the inorganic salt composition of ⅓ MS medium, to obtain a bacterial fluid. One hundred tissue sections obtained after the cultivation of *cyclamen* petioles were immersed in it for 30 minutes. After the treatment, the *cyclamen* petioles were removed from the bacterial fluid, and any excess bacterial fluid was absorbed with a sterilized filter paper. Subsequently, the petioles were cultivated in a co-culture medium for 7 days at 20° C. in the dark. The co-culture medium is a medium based on the inorganic component composition of MS medium and further containing sucrose at 5%, 2,4-D at 4 mg/L, kinetin at 0.1 mg/L, acetosyringone at 20 mg/L, and Gelrite at 0.3%.

The petioles infected as described above were cultured in a somatic embryogenesis medium prepared by adding antibiotic carbenicillin to be a concentration of 0.5 g/L for 60 days at 25° C. in the dark, while being subcultivated every 30 days, and thus *Agrobacterium* cells were completely removed. The somatic embryogenesis medium is a medium based on the inorganic component composition of MS medium and further containing sucrose at 5%, 2,4-D at 4 mg/L, kinetin at 0.1 mg/L, and Gelrite at 0.3%. After 60 days of cultivation, adventitious embryos were formed from the transformed calluses.

(6) Production of Transformed *Cyclamen*-2

Next, plants were regenerated from the adventitious embryos obtained as described above. Specifically, the adventitious embryos were bedded on a regeneration medium which was based on the inorganic component composition of MS medium and further contained sucrose at 3%, BA at 0.1 mg/L, naphthaleneacetic acid at 0.01 mg/L, gibberellin at 0.2 mg/L, and Gelrite at 0.5%, while the density of the adventitious embryos was adjusted to be 100 embryos per Petri dish. These were cultivated for 30 days at 25° C. in the dark, and were also cultivated while being illuminated with light at 10,000 lux for 16 hours per day. Thus, transformed regenerated plants were obtained. These regenerated plants (seedling plants) were transplanted into a test tube containing an MS medium containing sucrose at a concentration of 30 g/L and Gelrite at a concentration of 3 g/L. The transplanted seedling plants were cultivated, and twenty-four grown *cyclamen* plants (transformants of Fragrance Mini Amethyst Blue) were obtained.

(7) Evaluation of Cultivation of Transformed *Cyclamen*-2

With regard to the transformed *cyclamen* obtained as described above, the leaves were used as a material for genetic analysis, and it was confirmed by PCR that both a fusion gene of CpAG1 gene and a gene encoding SRDX, and a fusion gene of CpAG2 gene and a gene encoding SRDX had been introduced.

In the transformants of Fragrance Mini Amethyst Blue obtained as described above, stamens and pistils had been converted to petals, similarly to the case of the Wink Pink transformed with CpAG2SRDX, and thus the transformants exhibited a phenotype of markedly increased numbers of petals as compared to non-transformants.

The present invention is based on the discovery for the first time that *cyclamen* has functionally different two types of AG genes, and that when the function of at least one of those genes is inhibited in *cyclamen*, an excellent effect of significantly increasing the number of petals is obtained.

Comparative Example

Introduction of *Arabidopsis thaliana* AGAMOUS Gene into *Cyclamen*

From an *Arabidopsis thaliana* cDNA library (obtained from the National Institute of Advanced Industrial Science and Technology), a DNA fragment containing only the coding region of *Arabidopsis thaliana* AG gene (AtAG gene) except for the termination codon was amplified by PCR using an oligonucleotide having the nucleotide sequence of SEQ ID NO: 65 and an oligonucleotide having the nucleotide sequence of SEQ ID NO: 66 as a primer set.

Figure 3:
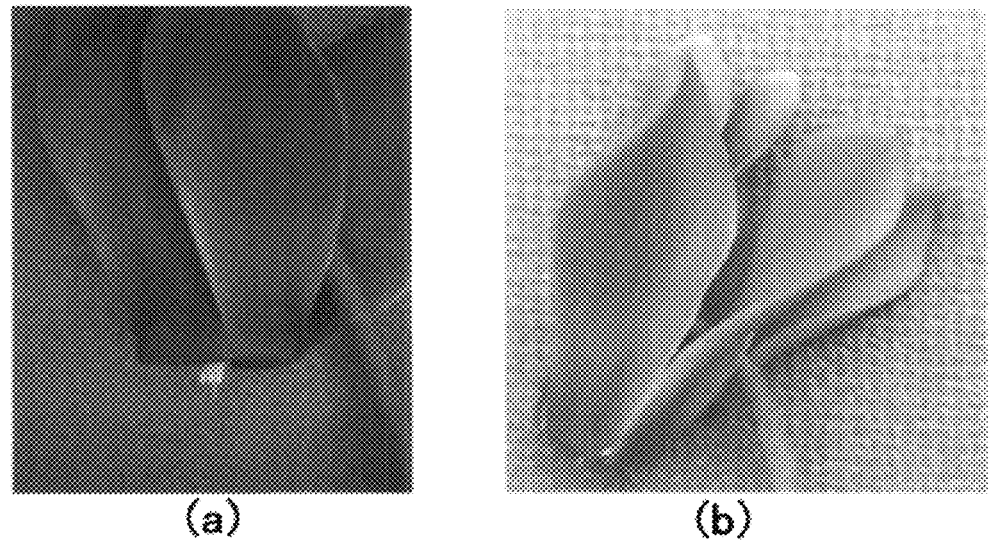
FIG. 3 illustrates the pictures of (a) the floral organs of a Fragrance Mini which has been transformed with AtAG-SRDX; and (b) the floral organs of a Fragrance Mini which has not been transformed.

The DNA fragment of the coding region of AtAG gene thus obtained was ligated to the SmaI site of the above-described vector for construction, p35SSRDXG, which had been digested in advance with restriction enzyme SmaI. *E. coli* was transformed with this plasmid, and the plasmid was collected from the proliferated, transformed *E. coli*. Subsequently, the nucleotide sequence of the plasmid was determined, and thereby a clone having the insert in the forward direction was selected. Thus, a vector in which a chimeric gene of AtAG gene and a gene encoding SRDX had been incorporated, p35SAtAGSRDX, was obtained. Subsequently, a vector for plant transformation, p35AtAGSRDX, was constructed by the same method as that used in the Examples, and this vector was introduced into *cyclamen* (variety: Fragrance Mini). Thereby, eleven transformed *cyclamen* plants were obtained. The results of a comparison made between the phenotype of the *cyclamen* that had been transformed with AtAGSRDX and the phenotype that had not been transformed, are presented in FIG. 3. As is obvious from FIG. 3, an increase in the number of petals was not recognized in the *cyclamen* transformed with AtAGSRDX.

INDUSTRIAL APPLICABILITY

According to the present invention, a *cyclamen* having an increased number of petals can be obtained, and thereby the decorative properties of *cyclamen* can be improved. Therefore, the present invention is useful in the fields of horticulture, agriculture, and agribusiness.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2009-286703 filed in Japan on Dec. 17, 2009, which is entirely herein incorporated by reference.

The invention claimed is:

1. A method of producing a *cyclamen* plant having an increased number of petals, comprising (i) inhibiting the functions of CpAG1 and CpAG2 in the plant, wherein the inhibiting comprises introducing a construct encoding a chimeric protein comprising CpAG1 fused to an SRDX domain and a construct encoding a chimeric protein comprising CpAG2 fused to an SRDX domain into the *cyclamen* plant; and (ii) selecting a resulting plant that is multi-petaled and has an increased number of petals as compared to a *cyclamen* plant having only CpAG1 activity inhibited, wherein the CpAG1 comprises the amino acid sequence defined in any one of the following (a) to (b):
   (a) the amino acid sequence of SEQ ID NO: 2, and
   (b) an amino acid sequence sharing 95% or more identity with the amino acid sequence of SEQ ID NO: 2, and
   wherein the CpAG2 comprises the amino acid sequence defined in any one of the following (c) to (d):
   (c) the amino acid sequence of SEQ ID NO: 4, and
   (d) an amino acid sequence sharing 95% or more identity with the amino acid sequence of SEQ ID NO: 4.

2. A method of producing a multi-petaled *cyclamen* plant having an increased number of petals, comprising (i) inhibiting the function of CpAG2 in a mutant *cyclamen* plant in which the function of CpAG1 is inhibited, wherein the inhibiting comprises introducing a construct encoding a chimeric protein comprising CpAG2 fused to an SRDX domain, wherein the CpAG2 comprises the amino acid sequence defined in any one of the following (c) to (d):
   (c) the amino acid sequence of SEQ ID NO: 4, and
   (d) an amino acid sequence sharing 95% or more identity with the amino acid sequence of SEQ ID NO: 4,
   wherein CpAG1 comprises the amino acid sequence defined in any one of the following (a) to (b):
   (a) the amino acid sequence of SEQ ID NO: 2, and
   (b) an amino acid sequence sharing 95% or more identity with the amino acid sequence of SEQ ID NO: 2; and
   (ii) selecting a resulting plant that is multi-petaled and has an increased number of petals as compared to the mutant *cyclamen* plant.

3. The production method according to claim 1, wherein the SRDX domain is a peptide comprising any one of the amino acid sequences of SEQ ID NOS: 5 to 44.

4. A *cyclamen* plant produced by the production method according to claim 1.

* * * * *

SEQUENCE LISTING

```
<160> NUMBER OF SEQ ID NOS: 66

<210> SEQ ID NO 1
<211> LENGTH: 1083
<212> TYPE: DNA
<213> ORGANISM: Cyclamen persicum
<220> FEATURE:
<221> NAME/KEY: CDS
<222> LOCATION: (111)..(851)

<400> SEQUENCE: 1
atatcaattt atcatctctc aactgttcat ttacatgaat tagaggagag gccaagtgaa      60
gatattcttt agggctcatt tcccccttttt atcaaaacca ggttgtggcg atg gag      116
                                                          Met Glu
                                                            1 ttt cca cac gat tca atg gac gtc tcc gat agg aaa ttt gcc agg ggg      164
Phe Pro His Asp Ser Met Asp Val Ser Asp Arg Lys Phe Ala Arg Gly
        5                  10                  15 aaa att gag atc aag cgg atc gaa aac acg acg aat cgc cag gtc acc      212
Lys Ile Glu Ile Lys Arg Ile Glu Asn Thr Thr Asn Arg Gln Val Thr
 20                  25                  30 ttc tgt aaa cgc cgc aat gga ttg ctc aag aaa gcc tat gaa ttg tcg      260
Phe Cys Lys Arg Arg Asn Gly Leu Leu Lys Lys Ala Tyr Glu Leu Ser
 35                  40                  45                  50 gtt ctt tgt gat gcc gag att gct ctt att gtg ttc tct aac cga ggc      308
Val Leu Cys Asp Ala Glu Ile Ala Leu Ile Val Phe Ser Asn Arg Gly
                 55                  60                  65 cgc ctt tat gag tac tcc aac aac agt gtc aaa gca aca ata cag agg      356
Arg Leu Tyr Glu Tyr Ser Asn Asn Ser Val Lys Ala Thr Ile Gln Arg
             70                  75                  80 tac aag aag gca acc tca gac tcc ggt gct gga tcg gtc tcc gag cta      404
Tyr Lys Lys Ala Thr Ser Asp Ser Gly Ala Gly Ser Val Ser Glu Leu
         85                  90                  95 aat gct cag ttc tat caa caa gaa gct gct aaa ttg cga gca caa atc      452
Asn Ala Gln Phe Tyr Gln Gln Glu Ala Ala Lys Leu Arg Ala Gln Ile
    100                 105                 110 ggg aat ttg gag aac tcc aac agg aac atg cgc ggt gaa tct ctt tgc      500
Gly Asn Leu Glu Asn Ser Asn Arg Asn Met Arg Gly Glu Ser Leu Cys
115                 120                 125                 130 tcg tta ccc atg agg gac ctg aag aac ctg gag act aaa ttg gag aaa      548
Ser Leu Pro Met Arg Asp Leu Lys Asn Leu Glu Thr Lys Leu Glu Lys
                135                 140                 145 agc atc ggt aaa atc cgc tca aag aag aat gag ctc tta ttt gcc gaa      596
Ser Ile Gly Lys Ile Arg Ser Lys Lys Asn Glu Leu Leu Phe Ala Glu
            150                 155                 160
```

```
atc gat ctt atg caa aag agg gaa gtc gac ttg cat aac aat aac cag    644
Ile Asp Leu Met Gln Lys Arg Glu Val Asp Leu His Asn Asn Asn Gln
        165                 170                 175 tac ctt cga gca aag ata gct gag aat gag aga gtt caa cag cac cgg    692
Tyr Leu Arg Ala Lys Ile Ala Glu Asn Glu Arg Val Gln Gln His Arg
    180                 185                 190 caa atg aac ttg atg ccc ggg acc tcg gag tac gag ttg atg cag ccg    740
Gln Met Asn Leu Met Pro Gly Thr Ser Glu Tyr Glu Leu Met Gln Pro
195                 200                 205                 210 cca gct ccg caa tcg tca tac gat gct cgt aac tac ata caa gtt        788
Pro Ala Pro Gln Ser Ser Tyr Asp Ala Arg Asn Tyr Ile Gln Val
                215                 220                 225 aac ggt ctt caa ccc aat ctt ggt cac tac tct cac caa gac caa aca    836
Asn Gly Leu Gln Pro Asn Leu Gly His Tyr Ser His Gln Asp Gln Thr
            230                 235                 240 ctc ctt cag cta ggt taataataag ctggaagaat ggtagatttc ttttgtggaa    891
Leu Leu Gln Leu Gly
        245 acttctccat gtttatcgtt gtattattat gtttcgaact ttttatatcg gtggacagta   951 acgaatctat ccgtctcgtg cttgtattcg atgtatgttt tctctatgaa attgtaactt  1011 cataaacttc gcaagtcctt cgtcaactat gcattttagt gatattctat ttgttaaaa   1071 aaaaaaaaaa aa                                                       1083

<210> SEQ ID NO 2
<211> LENGTH: 247
<212> TYPE: PRT
<213> ORGANISM: Cyclamen persicum

<400> SEQUENCE: 2

Met Glu Phe Pro His Asp Ser Met Asp Val Ser Asp Arg Lys Phe Ala
1               5                   10                  15

Arg Gly Lys Ile Glu Ile Lys Arg Ile Glu Asn Thr Thr Asn Arg Gln
            20                  25                  30

Val Thr Phe Cys Lys Arg Arg Asn Gly Leu Leu Lys Lys Ala Tyr Glu
        35                  40                  45

Leu Ser Val Leu Cys Asp Ala Glu Ile Ala Leu Ile Val Phe Ser Asn
    50                  55                  60

Arg Gly Arg Leu Tyr Glu Tyr Ser Asn Asn Ser Val Lys Ala Thr Ile
65                  70                  75                  80

Gln Arg Tyr Lys Lys Ala Thr Ser Asp Ser Gly Ala Gly Ser Val Ser
                85                  90                  95

Glu Leu Asn Ala Gln Phe Tyr Gln Gln Glu Ala Ala Lys Leu Arg Ala
            100                 105                 110

Gln Ile Gly Asn Leu Glu Asn Ser Asn Arg Asn Met Arg Gly Glu Ser
        115                 120                 125

Leu Cys Ser Leu Pro Met Arg Asp Leu Lys Asn Leu Glu Thr Lys Leu
    130                 135                 140

Glu Lys Ser Ile Gly Lys Ile Arg Ser Lys Lys Asn Glu Leu Leu Phe
145                 150                 155                 160

Ala Glu Ile Asp Leu Met Gln Lys Arg Glu Val Asp Leu His Asn Asn
                165                 170                 175

Asn Gln Tyr Leu Arg Ala Lys Ile Ala Glu Asn Glu Arg Val Gln Gln
            180                 185                 190

His Arg Gln Met Asn Leu Met Pro Gly Thr Ser Glu Tyr Glu Leu Met
        195                 200                 205
```

```
Gln Pro Pro Ala Pro Gln Ser Ser Tyr Asp Ala Arg Asn Tyr Ile
    210                 215                 220

Gln Val Asn Gly Leu Gln Pro Asn Leu Gly His Tyr Ser His Gln Asp
225                 230                 235                 240

Gln Thr Leu Leu Gln Leu Gly
                245

<210> SEQ ID NO 3
<211> LENGTH: 1073
<212> TYPE: DNA
<213> ORGANISM: Cyclamen persicum
<220> FEATURE:
<221> NAME/KEY: CDS
<222> LOCATION: (87)..(830)

<400> SEQUENCE: 3
attatcttct cttcaatttc atgttcatga attagagata tgctttaggt ctcatctccc    60
tatcttgcca aaaccaggtt gtggcg atg gag ttt cca cac gat tca atg gac   113
                            Met Glu Phe Pro His Asp Ser Met Asp
                            1               5 ctt tct gat aag aat aaa ctg ggg cgg gga aaa att gag atc aag cgg   161
Leu Ser Asp Lys Asn Lys Leu Gly Arg Gly Lys Ile Glu Ile Lys Arg
10              15                  20                  25 atc gaa aac acg acg aat cgc cag gtc acc ttt tgt aaa cgc cgc aac   209
Ile Glu Asn Thr Thr Asn Arg Gln Val Thr Phe Cys Lys Arg Arg Asn
            30                  35                  40 gga ttg ctc aag aaa gcc tat gaa ttg tcg gtt ctt tgt gat gcc gag   257
Gly Leu Leu Lys Lys Ala Tyr Glu Leu Ser Val Leu Cys Asp Ala Glu
        45                  50                  55 gtt gct ctt gtt gtc ttc tca aac cga ggc cgc ctt tat gag tac tcc   305
Val Ala Leu Val Val Phe Ser Asn Arg Gly Arg Leu Tyr Glu Tyr Ser
    60                  65                  70 aac agc agt gtc aaa gca aca ata cag agg tac aag aag gca act tca   353
Asn Ser Ser Val Lys Ala Thr Ile Gln Arg Tyr Lys Lys Ala Thr Ser
75                  80                  85 gac act agt gct gga tcg gtc tct gaa ctt aac gca cag tat tat caa   401
Asp Thr Ser Ala Gly Ser Val Ser Glu Leu Asn Ala Gln Tyr Tyr Gln
90                  95                  100                 105 caa gaa gct gct aaa ctg cga gcg caa att ggg aat ttg gag aac tcc   449
Gln Glu Ala Ala Lys Leu Arg Ala Gln Ile Gly Asn Leu Glu Asn Ser
            110                 115                 120 aac agg aac atg cgg ggt gaa tct ctg tgc tcg ttg ccg atg agg gac   497
Asn Arg Asn Met Arg Gly Glu Ser Leu Cys Ser Leu Pro Met Arg Asp
        125                 130                 135 ctg aag aac ctg gaa gct aaa ttg gag aaa agt att agt aaa atc cgc   545
Leu Lys Asn Leu Glu Ala Lys Leu Glu Lys Ser Ile Ser Lys Ile Arg
    140                 145                 150 tca aag aag aat gag ctc tta ttt gcc gaa ctc gat ctt atg cag aag   593
Ser Lys Lys Asn Glu Leu Leu Phe Ala Glu Leu Asp Leu Met Gln Lys
155                 160                 165 agg gaa gtc gac ttg cat agc aat aac caa tac ctt cgt gca aag ata   641
Arg Glu Val Asp Leu His Ser Asn Asn Gln Tyr Leu Arg Ala Lys Ile
170                 175                 180                 185 gcg gag agc gaa aga gct caa cag cac cag caa atg aac ttg atg tct   689
Ala Glu Ser Glu Arg Ala Gln Gln His Gln Gln Met Asn Leu Met Ser
            190                 195                 200 ggg agt tcg gag tac gag ctg atg caa cca cca gct cag cag tcg tca   737
Gly Ser Ser Glu Tyr Glu Leu Met Gln Pro Pro Ala Gln Gln Ser Ser
        205                 210                 215
```

```
tca tac gat gct cgt aac tac ata caa ctg aat ggt ctt cca ccc gat       785
Ser Tyr Asp Ala Arg Asn Tyr Ile Gln Leu Asn Gly Leu Pro Pro Asp
        220                 225                 230 ctt ggt cac tac tct cac caa gac caa aca ctc ctt caa cta ggg           830
Leu Gly His Tyr Ser His Gln Asp Gln Thr Leu Leu Gln Leu Gly
    235                 240                 245 taatgtgaac gacaacgacc ttctatacac gaatttaagt gccaccatta tctaatatat     890
atagacaata tgcatctact aatgcaagga aaatacttttt attgtaaaat tataacacct    950
tcgttggttg ttaaacaaaa aatactgtgc gaaaactatt accttgttca tattcggatc    1010
actgttgaag acgagtttta tcgatagaag tgatggatta tccttgaaaa aaaaaaaaaa    1070
aaa                                                                  1073

<210> SEQ ID NO 4
<211> LENGTH: 248
<212> TYPE: PRT
<213> ORGANISM: Cyclamen persicum

<400> SEQUENCE: 4

Met Glu Phe Pro His Asp Ser Met Asp Leu Ser Asp Lys Asn Lys Leu
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Val Phe Ser
    50                  55                  60

Asn Arg Gly Arg Leu Tyr Glu Tyr Ser Asn Ser Ser Val Lys Ala Thr
65                  70                  75                  80

Ile Gln Arg Tyr Lys Lys Ala Thr Ser Asp Thr Ser Ala Gly Ser Val
                85                  90                  95

Ser Glu Leu Asn Ala Gln Tyr Tyr Gln Gln Glu Ala Ala Lys Leu Arg
            100                 105                 110

Ala Gln Ile Gly Asn Leu Glu Asn Ser Asn Arg Asn Met Arg Gly Glu
        115                 120                 125

Ser Leu Cys Ser Leu Pro Met Arg Asp Leu Lys Asn Leu Glu Ala Lys
    130                 135                 140

Leu Glu Lys Ser Ile Ser Lys Ile Arg Ser Lys Lys Asn Glu Leu Leu
145                 150                 155                 160

Phe Ala Glu Leu Asp Leu Met Gln Lys Arg Glu Val Asp Leu His Ser
                165                 170                 175

Asn Asn Gln Tyr Leu Arg Ala Lys Ile Ala Glu Ser Glu Arg Ala Gln
            180                 185                 190

Gln His Gln Gln Met Asn Leu Met Ser Gly Ser Ser Tyr Glu Leu
        195                 200                 205

Met Gln Pro Pro Ala Gln Ser Ser Ser Tyr Asp Ala Arg Asn Tyr
    210                 215                 220

Ile Gln Leu Asn Gly Leu Pro Pro Asp Leu Gly His Tyr Ser His Gln
225                 230                 235                 240

Asp Gln Thr Leu Leu Gln Leu Gly
                245

<210> SEQ ID NO 5
<211> LENGTH: 12
<212> TYPE: PRT
<213> ORGANISM: Artificial sequence
```

```
<220> FEATURE:
<223> OTHER INFORMATION: Synthetic peptide

<400> SEQUENCE: 5

Asp Leu Asp Leu Asn Leu Ala Pro Pro Met Glu Phe
1               5                   10

<210> SEQ ID NO 6
<211> LENGTH: 11
<212> TYPE: PRT
<213> ORGANISM: Artificial sequence
<220> FEATURE:
<223> OTHER INFORMATION: Synthetic peptide

<400> SEQUENCE: 6

Leu Asp Leu Asn Leu Ala Pro Pro Met Glu Phe
1               5                   10

<210> SEQ ID NO 7
<211> LENGTH: 11
<212> TYPE: PRT
<213> ORGANISM: Artificial sequence
<220> FEATURE:
<223> OTHER INFORMATION: Synthetic peptide

<400> SEQUENCE: 7

Leu Asp Leu Asn Leu Ala Ala Ala Ala Ala Ala
1               5                   10

<210> SEQ ID NO 8
<211> LENGTH: 10
<212> TYPE: PRT
<213> ORGANISM: Artificial sequence
<220> FEATURE:
<223> OTHER INFORMATION: Synthetic peptide

<400> SEQUENCE: 8

Leu Asp Leu Glu Leu Arg Leu Gly Phe Ala
1               5                   10

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Asp Leu Glu Leu Arg Leu
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic peptide

<400> SEQUENCE: 10

Leu Asp Leu Gln Leu Arg Leu Gly Tyr Tyr
1               5                   10

<210> SEQ ID NO 11
<211> LENGTH: 7
<212> TYPE: PRT
<213> ORGANISM: Artificial sequence
<220> FEATURE:
```

```
<223> OTHER INFORMATION: Synthetic peptide

<400> SEQUENCE: 11

Leu Asp Leu Glu Leu Arg Leu
1               5

<210> SEQ ID NO 12
<211> LENGTH: 11
<212> TYPE: PRT
<213> ORGANISM: Artificial sequence
<220> FEATURE:
<223> OTHER INFORMATION: Synthetic peptide

<400> SEQUENCE: 12

Leu Asp Leu Glu Leu Ala Ala Ala Ala Ala
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13

Leu Asp Leu Glu Leu Arg Leu Ala Ala Ala
1               5                   10

<210> SEQ ID NO 14
<211> LENGTH: 8
<212> TYPE: PRT
<213> ORGANISM: Artificial sequence
<220> FEATURE:
<223> OTHER INFORMATION: Synthetic peptide

<400> SEQUENCE: 14

Leu Asp Leu Glu Leu Arg Leu Gly
1               5

<210> SEQ ID NO 15
<211> LENGTH: 11
<212> TYPE: PRT
<213> ORGANISM: Artificial sequence
<220> FEATURE:
<223> OTHER INFORMATION: Synthetic peptide

<400> SEQUENCE: 15

Phe Asp Leu Asn Phe Ala Pro Leu Asp Cys Val
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic peptide

<400> SEQUENCE: 16

Phe Asp Leu Asn Ile Pro Pro Ile Pro Glu Phe
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic peptide
```

<400> SEQUENCE: 17

Phe Gln Phe Asp Leu Asn Phe Pro Pro Leu Asp Cys Val
1               5                   10

<210> SEQ ID NO 18
<211> LENGTH: 6
<212> TYPE: PRT
<213> ORGANISM: Artificial sequence
<220> FEATURE:
<223> OTHER INFORMATION: Synthetic peptide

<400> SEQUENCE: 18

Asp Leu Asp Leu Arg Leu
1               5

<210> SEQ ID NO 19
<211> LENGTH: 35
<212> TYPE: PRT
<213> ORGANISM: Artificial sequence
<220> FEATURE:
<223> OTHER INFORMATION: Synthetic peptide

<400> SEQUENCE: 19

Val Gly Pro Thr Val Ser Asp Ser Ser Ser Ala Val Glu Glu Asn Gln
1               5                   10                  15

Tyr Asp Gly Lys Arg Gly Ile Asp Leu Asp Leu Asn Leu Ala Pro Pro
            20                  25                  30

Met Glu Phe
        35

<210> SEQ ID NO 20
<211> LENGTH: 11
<212> TYPE: PRT
<213> ORGANISM: Artificial sequence
<220> FEATURE:
<223> OTHER INFORMATION: Synthetic peptide

<400> SEQUENCE: 20

Asp Leu Asp Leu Glu Leu Arg Leu Gly Phe Ala
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetic peptide

<400> SEQUENCE: 21

Leu Asp Leu Asp Leu Glu Leu Arg Leu Gly Phe Ala
1               5                   10

<210> SEQ ID NO 22
<211> LENGTH: 204
<212> TYPE: PRT
<213> ORGANISM: Arabidopsis thaliana

<400> SEQUENCE: 22

Met Glu Arg Ser Asn Ser Ile Glu Leu Arg Asn Ser Phe Tyr Gly Arg
1               5                   10                  15

Ala Arg Thr Ser Pro Trp Ser Tyr Gly Asp Tyr Asp Asn Cys Gln Gln
            20                  25                  30

Asp His Asp Tyr Leu Leu Gly Phe Ser Trp Pro Pro Arg Ser Tyr Thr

```
                35                  40                  45
Cys Ser Phe Cys Lys Arg Glu Phe Arg Ser Ala Gln Ala Leu Gly Gly
         50                  55                  60

His Met Asn Val His Arg Arg Asp Arg Ala Arg Leu Arg Leu Gln Gln
 65                  70                  75                  80

Ser Pro Ser Ser Ser Thr Pro Ser Pro Tyr Pro Asn Pro Asn
                 85                  90                  95

Tyr Ser Tyr Ser Thr Met Ala Asn Ser Pro Pro His His Ser Pro
                100                 105                 110

Leu Thr Leu Phe Pro Thr Leu Ser Pro Pro Ser Ser Pro Arg Tyr Arg
                115                 120                 125

Ala Gly Leu Ile Arg Ser Leu Ser Pro Lys Ser Lys His Thr Pro Glu
                130                 135                 140

Asn Ala Cys Lys Thr Lys Lys Ser Ser Leu Leu Val Glu Ala Gly Glu
145                 150                 155                 160

Ala Thr Arg Phe Thr Ser Lys Asp Ala Cys Lys Ile Leu Arg Asn Asp
                165                 170                 175

Glu Ile Ile Ser Leu Glu Leu Glu Ile Gly Leu Ile Asn Glu Ser Glu
                180                 185                 190

Gln Asp Leu Asp Leu Glu Leu Arg Leu Gly Phe Ala
                195                 200
```

```
<210> SEQ ID NO 23
<211> LENGTH: 30
<212> TYPE: PRT
<213> ORGANISM: Artificial sequence
<220> FEATURE:
<223> OTHER INFORMATION: Synthetic peptide

<400> SEQUENCE: 23

Asn Asp Glu Ile Ile Ser Leu Glu Leu Glu Ile Gly Leu Ile Asn Glu
1               5                   10                  15

Ser Glu Gln Asp Leu Asp Leu Glu Leu Arg Leu Gly Phe Ala
            20                  25                  30

<210> SEQ ID NO 24
<211> LENGTH: 6
<212> TYPE: PRT
<213> ORGANISM: Artificial sequence
<220> FEATURE:
<223> OTHER INFORMATION: Synthetic peptide

<400> SEQUENCE: 24

Asp Leu Asn Leu Arg Leu
1               5

<210> SEQ ID NO 25
<211> LENGTH: 6
<212> TYPE: PRT
<213> ORGANISM: Artificial sequence
<220> FEATURE:
<223> OTHER INFORMATION: Synthetic peptide

<400> SEQUENCE: 25

Asp Leu Asp Leu Arg Leu
1               5

<210> SEQ ID NO 26
<211> LENGTH: 6
<212> TYPE: PRT
<213> ORGANISM: Artificial sequence
```

<220> FEATURE:
<223> OTHER INFORMATION: Synthetic peptide

<400> SEQUENCE: 26

Asp Leu Gln Leu Arg Leu
1               5

<210> SEQ ID NO 27
<211> LENGTH: 6
<212> TYPE: PRT
<213> ORGANISM: Artificial sequence
<220> FEATURE:
<223> OTHER INFORMATION: Synthetic peptide

<400> SEQUENCE: 27

Asp Leu Arg Leu Arg Leu
1               5

<210> SEQ ID NO 28
<211> LENGTH: 6
<212> TYPE: PRT
<213> ORGANISM: Artificial sequence
<220> FEATURE:
<223> OTHER INFORMATION: Synthetic peptide

<400> SEQUENCE: 28

Glu Leu Glu Leu Arg Leu
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic peptide

<400> SEQUENCE: 29

Asn Leu Glu Leu Arg Leu
1               5

<210> SEQ ID NO 30
<211> LENGTH: 6
<212> TYPE: PRT
<213> ORGANISM: Artificial sequence
<220> FEATURE:
<223> OTHER INFORMATION: Synthetic peptide

<400> SEQUENCE: 30

Gln Leu Glu Leu Arg Leu
1               5

<210> SEQ ID NO 31
<211> LENGTH: 6
<212> TYPE: PRT
<213> ORGANISM: Artificial sequence
<220> FEATURE:
<223> OTHER INFORMATION: Synthetic peptide

<400> SEQUENCE: 31

Asp Leu Glu Leu Asn Leu
1               5

<210> SEQ ID NO 32
<211> LENGTH: 6
<212> TYPE: PRT
<213> ORGANISM: Artificial sequence
<220> FEATURE:

```
<223> OTHER INFORMATION: Synthetic peptide

<400> SEQUENCE: 32

Asp Leu Glu Leu Gln Leu
1               5

<210> SEQ ID NO 33
<211> LENGTH: 6
<212> TYPE: PRT
<213> ORGANISM: Artificial sequence
<220> FEATURE:
<223> OTHER INFORMATION: Synthetic peptide

<400> SEQUENCE: 33

Thr Leu Glu Leu Arg Leu
1               5

<210> SEQ ID NO 34
<211> LENGTH: 6
<212> TYPE: PRT
<213> ORGANISM: Artificial sequence
<220> FEATURE:
<223> OTHER INFORMATION: Synthetic peptide

<400> SEQUENCE: 34

Asp Leu Glu Leu Thr Leu
1               5

<210> SEQ ID NO 35
<211> LENGTH: 6
<212> TYPE: PRT
<213> ORGANISM: Artificial sequence
<220> FEATURE:
<223> OTHER INFORMATION: Synthetic peptide

<400> SEQUENCE: 35

Ser Leu Glu Leu Arg Leu
1               5

<210> SEQ ID NO 36
<211> LENGTH: 6
<212> TYPE: PRT
<213> ORGANISM: Artificial sequence
<220> FEATURE:
<223> OTHER INFORMATION: Synthetic peptide

<400> SEQUENCE: 36

Asp Leu Glu Leu Ser Leu
1               5

<210> SEQ ID NO 37
<211> LENGTH: 6
<212> TYPE: PRT
<213> ORGANISM: Artificial sequence
<220> FEATURE:
<223> OTHER INFORMATION: Synthetic peptide

<400> SEQUENCE: 37

Asp Leu Thr Leu Arg Leu
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic peptide
```

<400> SEQUENCE: 38

Asp Leu Ser Leu Arg Leu
1               5

<210> SEQ ID NO 39
<211> LENGTH: 6
<212> TYPE: PRT
<213> ORGANISM: Artificial sequence
<220> FEATURE:
<223> OTHER INFORMATION: Synthetic peptide

<400> SEQUENCE: 39

Asp Leu His Leu Arg Leu
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic peptide

<400> SEQUENCE: 40

Ser Leu Asp Leu His Leu
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic peptide

<400> SEQUENCE: 41

Asp Leu Thr Leu Lys Leu
1               5

<210> SEQ ID NO 42
<211> LENGTH: 6
<212> TYPE: PRT
<213> ORGANISM: Artificial sequence
<220> FEATURE:
<223> OTHER INFORMATION: Synthetic peptide

<400> SEQUENCE: 42

Asp Leu Ser Leu Lys Leu
1               5

<210> SEQ ID NO 43
<211> LENGTH: 6
<212> TYPE: PRT
<213> ORGANISM: Artificial sequence
<220> FEATURE:
<223> OTHER INFORMATION: Synthetic peptide

<400> SEQUENCE: 43

Asp Leu Glu Phe Arg Leu
1               5

<210> SEQ ID NO 44
<211> LENGTH: 6
<212> TYPE: PRT
<213> ORGANISM: Artificial sequence
<220> FEATURE:
<223> OTHER INFORMATION: Synthetic peptide

```
<400> SEQUENCE: 44

Asp Phe Glu Leu Arg Leu
1               5

<210> SEQ ID NO 45
<211> LENGTH: 27
<212> TYPE: DNA
<213> ORGANISM: Artificial sequence
<220> FEATURE:
<223> OTHER INFORMATION: Synthetic primer

<400> SEQUENCE: 45
gatygagatc aarmggatcg aaaacac                                          27

<210> SEQ ID NO 46
<211> LENGTH: 26
<212> TYPE: DNA
<213> ORGANISM: Artificial sequence
<220> FEATURE:
<223> OTHER INFORMATION: Synthetic primer

<400> SEQUENCE: 46
tctgtkctyt gtgatgctga rgttgc                                           26

<210> SEQ ID NO 47
<211> LENGTH: 27
<212> TYPE: DNA
<213> ORGANISM: Artificial sequence
<220> FEATURE:
<223> OTHER INFORMATION: Synthetic primer

<400> SEQUENCE: 47
ttcyctytty tgcatgtact cratttc                                          27

<210> SEQ ID NO 48
<211> LENGTH: 24
<212> TYPE: DNA
<213> ORGANISM: Artificial sequence
<220> FEATURE:
<223> OTHER INFORMATION: Synthetic primer

<400> SEQUENCE: 48
ttagtctcca ggttcttcag gtcc                                             24

<210> SEQ ID NO 49
<211> LENGTH: 23
<212> TYPE: DNA
<213> ORGANISM: Artificial sequence
<220> FEATURE:
<223> OTHER INFORMATION: Synthetic primer

<400> SEQUENCE: 49
atcaaaacca ggttgtggcg atg                                              23

<210> SEQ ID NO 50
<211> LENGTH: 28
<212> TYPE: DNA
<213> ORGANISM: Artificial sequence
<220> FEATURE:
<223> OTHER INFORMATION: Synthetic primer

<400> SEQUENCE: 50
tcactaaaat gcatagttga cgaaggac                                         28

<210> SEQ ID NO 51
```

```
<211> LENGTH: 25
<212> TYPE: DNA
<213> ORGANISM: Artificial sequence
<220> FEATURE:
<223> OTHER INFORMATION: Synthetic primer

<400> SEQUENCE: 51
ctttctgata agaataaact ggggc                                    25

<210> SEQ ID NO 52
<211> LENGTH: 20
<212> TYPE: DNA
<213> ORGANISM: Artificial sequence
<220> FEATURE:
<223> OTHER INFORMATION: Synthetic primer

<400> SEQUENCE: 52
ctgaacttaa cgcacagtat                                          20

<210> SEQ ID NO 53
<211> LENGTH: 30
<212> TYPE: DNA
<213> ORGANISM: Artificial sequence
<220> FEATURE:
<223> OTHER INFORMATION: Synthetic primer

<400> SEQUENCE: 53
ttcgtgtata gaaggtcgtt gtcgttcaca                               30

<210> SEQ ID NO 54
<211> LENGTH: 25
<212> TYPE: DNA
<213> ORGANISM: Artificial sequence
<220> FEATURE:
<223> OTHER INFORMATION: Synthetic primer

<400> SEQUENCE: 54
agttagttac ttaagcttgg gcccc                                    25

<210> SEQ ID NO 55
<211> LENGTH: 30
<212> TYPE: DNA
<213> ORGANISM: Artificial sequence
<220> FEATURE:
<223> OTHER INFORMATION: Synthetic primer

<400> SEQUENCE: 55
gatccagtaa gcttaattgg ttccggcgcc                               30

<210> SEQ ID NO 56
<211> LENGTH: 23
<212> TYPE: DNA
<213> ORGANISM: Artificial sequence
<220> FEATURE:
<223> OTHER INFORMATION: Synthetic primer

<400> SEQUENCE: 56
tagaattcgc ggccgcactc gag                                      23

<210> SEQ ID NO 57
<211> LENGTH: 31
<212> TYPE: DNA
<213> ORGANISM: Artificial sequence
<220> FEATURE:
<223> OTHER INFORMATION: Synthetic primer

<400> SEQUENCE: 57
```

```
gagaattcgg gccagagctg cagctggatg g                                      31

<210> SEQ ID NO 58
<211> LENGTH: 82
<212> TYPE: DNA
<213> ORGANISM: Artificial sequence
<220> FEATURE:
<223> OTHER INFORMATION: Synthetic primer

<400> SEQUENCE: 58
ctagaggatc cacaattacc aacaacaaca aacaacaaac aacattacaa ttacagatcc       60 cggggggtacc gtcgacgagc tc                                              82

<210> SEQ ID NO 59
<211> LENGTH: 73
<212> TYPE: DNA
<213> ORGANISM: Artificial sequence
<220> FEATURE:
<223> OTHER INFORMATION: Synthetic primer

<400> SEQUENCE: 59
cgtcgacggt accccgggga tctgtaattg taatgttgtt tgttgtttgt tgttgttggt       60
aattgtggat cct                                                         73

<210> SEQ ID NO 60
<211> LENGTH: 43
<212> TYPE: DNA
<213> ORGANISM: Artificial sequence
<220> FEATURE:
<223> OTHER INFORMATION: Synthetic primer

<400> SEQUENCE: 60
gggcttgatc tggatctaga actccgtttg ggtttcgctt aag                        43

<210> SEQ ID NO 61
<211> LENGTH: 47
<212> TYPE: DNA
<213> ORGANISM: Artificial sequence
<220> FEATURE:
<223> OTHER INFORMATION: Synthetic primer

<400> SEQUENCE: 61
tcgacttaag cgaaacccaa acggagttct agatccagat caagccc                    47

<210> SEQ ID NO 62
<211> LENGTH: 24
<212> TYPE: DNA
<213> ORGANISM: Artificial sequence
<220> FEATURE:
<223> OTHER INFORMATION: Synthetic primer

<400> SEQUENCE: 62
atggagtttc cacacgattc aatg                                             24

<210> SEQ ID NO 63
<211> LENGTH: 24
<212> TYPE: DNA
<213> ORGANISM: Artificial sequence
<220> FEATURE:
<223> OTHER INFORMATION: Synthetic primer

<400> SEQUENCE: 63
acctagctga aggagtgttt ggtc                                             24
```

```
<210> SEQ ID NO 64
<211> LENGTH: 24
<212> TYPE: DNA
<213> ORGANISM: Artificial sequence
<220> FEATURE:
<223> OTHER INFORMATION: Synthetic primer

<400> SEQUENCE: 64
acctagttga aggagtgttt ggtc                                              24

<210> SEQ ID NO 65
<211> LENGTH: 29
<212> TYPE: DNA
<213> ORGANISM: Artificial sequence
<220> FEATURE:
<223> OTHER INFORMATION: Synthetic primer

<400> SEQUENCE: 65
atgaccgcgt accaatcgga gctaggagg                                         29

<210> SEQ ID NO 66
<211> LENGTH: 30
<212> TYPE: DNA
<213> ORGANISM: Artificial sequence
<220> FEATURE:
<223> OTHER INFORMATION: Synthetic primer

<400> SEQUENCE: 66
cactaactgg agagcggttt ggtcttggcg                                        30
```